US010335080B2

(12) United States Patent
Vaidyanathan et al.

(10) Patent No.: US 10,335,080 B2
(45) Date of Patent: Jul. 2, 2019

(54) BIOMECHANICAL ACTIVITY MONITORING

(71) Applicant: Imperial Innovations Limited, London (GB)

(72) Inventors: Ravi Vaidyanathan, London (GB); Niamh Nowlan, London (GB); Richard Woodward, London (GB); Sandra Shefelbine, London (GB)

(73) Assignee: Imperial Innovations Limited, London (GB)

( * ) Notice: Subject to any disclaimer, the term of this patent is extended or adjusted under 35 U.S.C. 154(b) by 315 days.

(21) Appl. No.: 15/034,165

(22) PCT Filed: Nov. 4, 2014

(86) PCT No.: PCT/GB2014/053276
§ 371 (c)(1),
(2) Date: May 3, 2016

(87) PCT Pub. No.: WO2015/063520
PCT Pub. Date: May 7, 2015

(65) Prior Publication Data
US 2016/0262687 A1    Sep. 15, 2016

(30) Foreign Application Priority Data

Nov. 4, 2013  (GB) .................... 1319434.5

(51) Int. Cl.
*A61B 5/00*    (2006.01)
*A61B 5/11*    (2006.01)
*A61B 5/0205*  (2006.01)
*A61B 7/00*    (2006.01)
*A61B 5/024*   (2006.01)
*A61B 5/08*    (2006.01)

(52) U.S. Cl.
CPC .......... *A61B 5/4519* (2013.01); *A61B 5/0205* (2013.01); *A61B 5/1107* (2013.01);
(Continued)

(58) Field of Classification Search
CPC ....... A61B 5/11; A61B 5/1107; A61B 5/1118; A61B 5/112; A61B 5/1126; A61B 5/0205; A61B 5/4519; A61B 5/7264
See application file for complete search history.

(56) References Cited

U.S. PATENT DOCUMENTS 6,344,062 B1     2/2002  Abboudi et al.
6,942,621 B2 *   9/2005  Avinash ............ A61B 5/02411
                                                      600/481

(Continued)

FOREIGN PATENT DOCUMENTS

EP    2 636 371 A1    9/2013
WO    1996/015713 A1  5/1996
WO    2013/151770 A1  10/2013

OTHER PUBLICATIONS

International Search Report and Written Opinion dated Feb. 17, 2015 for International Application No. PCT/GB2014/053276, filed on Nov. 4, 2014 (15 pages).

(Continued)

*Primary Examiner* — Max F Hindenburg
(74) *Attorney, Agent, or Firm* — Perkins Coie LLP

(57) ABSTRACT

A wearable sensor apparatus comprises a motion sensor configured to sense two or three dimensional movement and orientation of the sensor and a vibration sensor configured to sense acoustic vibrations. The apparatus includes means for attaching the motion sensor and the vibration sensor to a body. The sensor apparatus enables long term monitoring of mechanomyographic muscle activity in combination with body motion for a number of applications.

27 Claims, 15 Drawing Sheets

(52) U.S. Cl.
CPC .......... *A61B 5/1116* (2013.01); *A61B 5/1121* (2013.01); *A61B 5/1123* (2013.01); *A61B 5/4362* (2013.01); *A61B 5/4851* (2013.01); *A61B 5/7246* (2013.01); *A61B 5/7264* (2013.01); *A61B 7/006* (2013.01); *A61B 5/02411* (2013.01); *A61B 5/02444* (2013.01); *A61B 5/0816* (2013.01); *A61B 5/1126* (2013.01); *A61B 5/6802* (2013.01); *A61B 2503/02* (2013.01); *A61B 2503/10* (2013.01); *A61B 2503/12* (2013.01); *A61B 2505/09* (2013.01); *A61B 2560/0257* (2013.01); *A61B 2560/0475* (2013.01); *A61B 2562/0204* (2013.01); *A61B 2562/0219* (2013.01); *A61B 2562/0223* (2013.01); *A61B 2562/0247* (2013.01); *A61B 2562/164* (2013.01)

(56) References Cited

U.S. PATENT DOCUMENTS

| | | | |
|---|---|---|---|
| 7,787,946 B2 * | 8/2010 | Stahmann | A61B 5/0031 607/3 |
| 7,901,368 B2 * | 3/2011 | Flaherty | A61H 1/0255 601/33 |
| 9,597,015 B2 * | 3/2017 | McNames | A61B 5/1071 |
| 2009/0292194 A1 | 11/2009 | Libbus et al. | |
| 2010/0286572 A1 | 11/2010 | Moersdorf et al. | |
| 2010/0292617 A1 | 11/2010 | Lei et al. | |
| 2012/0265480 A1 | 10/2012 | Oshima | |
| 2013/0217998 A1 | 8/2013 | Mahfouz et al. | |

OTHER PUBLICATIONS

Mokaya, F., et al., "MARS: A Muscle Activity Recognition System Enabling Self-Configuring Musculoskeletal Sensor Networks," 2013 ACM/IEEE International Conference on Information Processing in Sensor Networks, pp. 191-202, Apr. 2013.

Silva, J., et al., "MMG-Based Multisensor Data Fusion for Prosthesis Control," Proceedings of the 25th Annual International Conference of the IEEE Engineering in Medicine and Biology Society, vol. 3, pp. 2909-2912, Sep. 2003.

UK Search Report dated May 2, 2014 for UK Patent Application No. 1319434.5, filed on Nov. 4, 2013 (3pages).

* cited by examiner

BIOMECHANICAL ACTIVITY MONITORING

The present invention relates to apparatus and methods for monitoring and/or analysing biomechanical activity in, for example, the human or animal body.

Monitoring human biomechanical activity is an important function in a diverse range of technical applications, including in both clinical and non-clinical environments. In the clinical environment, these functions may include health monitoring, such as for diagnosis, therapeutic intervention, rehabilitation, well-being and foetal monitoring etc. In the non-clinical environment, these functions may include providing human-machine interfaces, robot control, haptic systems and systems for use in sports training etc.

When providing combined muscle activity and motion recording, prior art systems have focused on monitoring muscle activity using electromyography (EMG) sensors, i.e. monitoring electrical activity produced by skeletal muscles. This technique can have significant disadvantages and has limited use outside well-controlled environments such as laboratories and clinical care establishments. Such electrical recording systems generally require single-use sensors (e.g. for clinical safety and hygiene reasons) and the use of adhesives and electrically conductive gel for attachment of the sensors to the body to ensure adequate electrical contact with the human subject. This imposes limitations on the practicality and ease of use of muscle activity sensing, on the environment of use, and on the duration of use. Thus detailed data acquired with such sensors may only be obtained for short periods of time, for a limited range of the subject's motion.

It is an object of the present invention to provide an alternative technique for monitoring and/or analysing biomechanical activity which reduces or mitigates some or all of these disadvantages.

According to one aspect, the present invention provides a wearable sensor apparatus comprising:

a motion sensor configured to sense two or three dimensional movement and orientation of the sensor;

a vibration sensor configured to sense acoustic vibrations; and means for attaching the motion sensor and the vibration sensor to a body.

The acoustic vibrations may be, or may be represented by, bioacoustic signals. The acoustic vibrations may be bioacoustic vibrations. The motion sensor may comprise an inertial measurement unit. The vibration sensor may be configured to sense skeletal muscle vibrations. The inertial measurement unit may comprise one or more of an accelerometer, a gyroscope, and a magnetometer. The inertial measurement unit may be configured to sense rotation of the sensor body around at least one axis in space. The inertial measurement unit may be capable of sensing translational motion in three perpendicular axes and/or rotation about three perpendicular axes. The vibration sensor may comprise an acoustic pressure sensor. The vibration sensor may comprise one or more of an accelerometer, a microphone, and a piezoelectric transducer. The vibration sensor may comprise a volumetric chamber closed at one end by a flexible membrane, and a pressure transducer coupled to the chamber distal from the flexible membrane. The apparatus may comprise a barometer. The barometer may be configured to sense an ambient pressure. The vibration sensor and the barometer may be provided by a single sensor.

The apparatus may further comprise a data logging device coupled to receive motion signals from the motion sensor and acoustic signals, such as muscle vibration signals or mechanomyographic (MMG) muscle signals, from the vibration sensor, and to store said signals as a function of time. The apparatus may further comprise a classification processor configured to receive motion signals from the motion sensor and to receive the muscle signals (or mechanomyographic muscle signals) from the vibration sensor, and to classify a pattern of movement, or a posture of, at least one part of a body on which the wearable sensor apparatus is attached. The classification processor may be configured to use both the motion signals and the muscle vibration signals (or mechanomyographic muscle signals) to determine simultaneous patterns of movement, or postures of, multiple articulating parts of the body on which the wearable sensor apparatus is attached. The muscle vibration signals may be mechanomyographic muscle signals. The classification processor may be configured to classify a pattern of movement, or a posture of, at least one part of a body on which the wearable sensor apparatus is attached based on the mechanomyographic muscle signals.

The classification processor may be configured to separate the signals from the vibration sensor into windowed data. The classification processor may be configured to perform cluster analysis on the windowed data to determine a correlation between the signals from the vibration sensor and a type of activity.

The cluster analysis may comprise determining clusters of the windowed data and comparing one or more properties of the clusters with one or more threshold values. A property of a cluster may be an averaged value of a property of the windowed data within the cluster. The one or more properties comprise one or more of: gyroscopic magnitude, peak gyroscopic magnitude, ambient pressure, a cadence of a user (which may be a number of steps taken in a unit of time) and orientation of the motion sensor.

The apparatus may comprise a classification processor configured to receive motion signals from the motion sensor, to receive an ambient pressure signal from the barometer and to receive signals from the vibration sensor, and to classify a pattern of movement, or a posture of, at least one part of a body on which the wearable sensor apparatus is attached based on the received signals.

The apparatus may further comprise a classification processor configured to receive motion signals from the motion sensor and to receive muscle vibration signals, such as mechanomyographic muscle signals, from the vibration sensor, and to classify a pattern of movement, or a posture of, at least one part of a body on which the wearable sensor apparatus is attached, based on said motion signals, and to identify muscular activity used during said pattern of movement or posture. The classification processor may be further configured to determine whether or not the identified muscular activity conforms to a predetermined pattern consistent with the classified pattern of movement.

The apparatus may further comprise a classification processor configured to receive motion signals from the motion sensor and to receive acoustic signals from the vibration sensor, and to determine when the acoustic signals correspond to foetal movement.

The apparatus may further include an interface module configured to provide output control signals for a computer processor based on the output of the classification processor. The apparatus may further include an interface module configured to provide output control signals for a motive apparatus based on the output of the classification processor. The apparatus may further include a said motive apparatus. The motive apparatus may comprise a prosthesis or a robotic device.

According to another aspect, the invention provides a method of classifying a pattern of movement, or a posture of, at least one part of a human or animal subject comprising the steps of:
- obtaining motion signals from a motion sensor attached to the subject, the motion signals being indicative of sensed movement of the subject in two or three dimensions;
- simultaneously obtaining vibration signals from a vibration sensor attached to the subject, the vibration signals being indicative of sensed skeletal muscle vibrations or other acoustic output from the subject; and
- using the motion signals and the sensed vibration signals, such as skeletal muscle vibration signals, to classify a pattern of movement, or a posture, of at least one part of the subject.

Other acoustic output from the subject may comprise acoustic output due to foetal movements. The method may further include using the motion signals and the sensed vibration signals to classify a pattern of movement, or a posture of, multiple articulating body parts of the subject. The method may further include using the motion signals and the sensed vibration signals to control movement of a computer processor or a motive apparatus. The vibration signals may be skeletal muscle vibration signals.

According to another aspect, the invention provides a method of assisting a human subject in rehabilitation comprising:
- obtaining motion signals from a motion sensor attached to the subject, the motion signals being indicative of sensed movement of the subject in two or three dimensions;
- simultaneously obtaining vibration signals from a vibration sensor attached to the subject, the vibration signals being indicative of sensed skeletal muscle vibrations or other acoustic output from the subject, such as a heart rate of, or breathing from, the subject; and
- classifying a pattern of movement, or a posture, of at least one part of the subject using at least the motion signals;
- determining whether the pattern of movement, or posture, of the at least one part of the subject conforms to a predetermined pattern of the sensed skeletal muscle vibration signals; and
- providing an audible or visual feedback to the user dependent on whether the pattern of movement, or posture, of the at least one part of the subject is consistent with the predetermined pattern of the sensed skeletal muscle vibration signals.

According to another aspect, the invention provides a method of monitoring a maternal body for foetal movement comprising:
- obtaining motion signals from a motion sensor attached to the maternal body, the motion signals being indicative of sensed movement of the subject in two or three dimensions;
- simultaneously obtaining acoustic vibration signals from one or more acoustic vibration sensors attached to the maternal body; and
- using at least the motion signals from the motion sensor to determine periods of maternal activity to attenuate or exclude maternal acoustic vibration signals from the vibration signals to thereby detect acoustic vibrations associated with foetal movement.

The acoustic vibration signals may be bioacoustic signals. The method may further comprise using acoustic vibration signals obtained from the acoustic vibration sensor to determine an orientation of a foetus. The method may further comprise using acoustic vibration signals obtained from the acoustic vibration sensor to generate a heart rate or a breathing rate from the maternal and/or foetal body.

Embodiments of the present invention will now be described by way of example and with reference to the accompanying drawings in which.

Mechanomyographic (MMG) muscle sensing exploits a low frequency vibration emitted by skeletal muscle the measurement of which does not require electrodes, gel or direct skin contact, unlike electromyographic sensing. This offers potential for much more efficient implementation in everyday use. Combining mechanomyographic muscle sensing with two- or three-dimensional movement sensing has been found to provide a considerable advance in human activity monitoring by combining human dynamics and muscle activity information. Bioacoustic sensors, such as MMG sensors, can readily be provided at relatively low cost, and can be packaged in a lightweight wearable package which is easy to attach to the subject's body without the use of complicated procedures for ensuring good electrical contact with the subject's skin.

In a general aspect, the techniques described here combine the use of inertial measurement units (IMUs) and acoustic sensors, e.g. bioacoustic sensors, such as mechanomyographic (MMG) sensors for muscle activity sensing or foetal movement monitoring. An arrangement described herein in relation to sensing a mechanomyographic muscle signal may also be used to sense bioacoustic signals or muscle vibration signals more generally.

Figure 1:
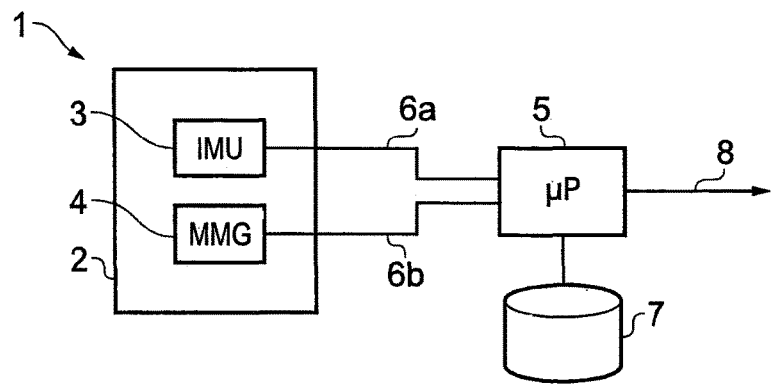
FIG. 1 shows a schematic diagram of a wearable activity sensor apparatus.

FIG. 1 shows a schematic diagram of a wearable activity sensor 1 comprising a support structure 2, a motion sensor 3 and a muscle vibration sensor 4. The support structure 2 may be any suitable structure for attachment to the human or animal body at an appropriate location. In one example, shown in FIG. 2, the support structure is a flexible, stretchable knee brace 20 with two motion sensors 3 sewn into pouches 21 with a muscle vibration sensor 4 having its membrane presented against the subject's skin on the inside surface of the support structure 20. Use of a flexible support structure 2 such as a knee brace 20 or a tubular bandage allows generally unhindered movement of the subject and suitability for extended periods of wear, e.g. over a whole day or several days. Many other forms of wearable activity sensor are possible, for example integrated into articles of clothing, and for attachment to any suitable part of the body such as arms, legs, hands, trunk etc. The activity sensors can be positioned on the body at any suitable location from which limb or body motion can be sensed, and from which vibrations from any target muscle groups can be detected. In another example, shown in FIG. 10 and discussed in more detail later, activity sensors may be provided on both sides of the subject's knee, i.e. on the upper leg and on the lower leg. Such an arrangement provides motion signals specific to both upper and lower parts of the leg and muscle vibration signals from both upper and lower leg. Such an arrangement is particularly useful in monitoring activity relating to walking, standing, sitting and lying down, gait and posture analysis, etc, as will be discussed further below.

The motion sensor 3 preferably comprises one or more Inertial Measurement Units (IMUs) which may consist of tri-axis gyroscopes and accelerometers and Magnetic Angular Rate and Gravity (MARG) sensor arrays that also include tri-axis magnetometers. In a general aspect, however, any motion sensor capable of sensing two- or three-dimensional translational movement of the sensor body in space and rotation of the sensor body around at least one axis in space can be used. Preferably, the motion sensor should be capable of sensing translational motion in three perpendicular axes (forward/backward, up/down, left/right) and rotation about three perpendicular axes (pitch, yaw and roll). However, it will be understood that certain types of motion tracking may not require all six degrees of freedom. MARG sensors are preferred due to their low cost, small size, light weight and accuracy.

The mechanomyographic muscle vibration sensor preferably comprises a pressure sensor. MMG muscle vibrations are low frequency vibrations emitted by skeletal muscle, believed to be the mechanical activity of muscle generated by lateral oscillations of muscle fibres. The MMG vibration sensor collects signals indicative of mechanical attributes of contracting muscles, such as fatigue. Unlike EMG sensors, MMG sensors do not require gel or direct skin contact and can be reused and readily applied by an unskilled user, for example, because the precision of placement required for an MMG sensor may be less stringent than for an EMG sensor.

The collection time of measurements using MMG sensors can be greater than that achieved using EMG sensors. The MMG vibration sensor may comprise one or more accelerometers, microphones, piezoelectric transducers, hydrophones or laser distance sensors. A preferred example is a pressure sensor in the form of a microphone sensor which provides very accurate results in detecting muscle activity and benefits by being little affected by motion noise. It is also easily integrated into a flexible support structure 2 as discussed above.

The MMG vibration sensor preferably provides a volumetric chamber with a membrane stretched over an opening in a housing of the chamber. A difference in volume of the volumetric chamber whenever the membrane is deformed by muscle vibration is detected using a microphone. When the membrane is placed over a subject's muscle, lateral contractions produce a physical change in the muscle's form, which in turn changes the membrane position and/or profile and creates a pressure change within the chamber. The microphone signals of particular interest lie between 1 and 256 Hz and are therefore preferably sampled at between 0.5 and 1 kHz. The signal may be boosted using an operational amplifier-based preamplifier which increases the power of the signal by a factor of approximately 21 times, specifically in the range of 1 Hz to 1 kHz which is sufficient for an MMG signal that has a dominant frequency in the range 25±2.5 Hz.

With further reference to FIG. 1, the wearable activity sensor 1 is coupled to a microprocessor 5 configured to receive motion signals from the motion sensor 3 via communication link 6a and to receive muscle vibration signals from the vibration sensor 4 via communication link 6b. The communication links 6a, 6b can be wired links or wireless links. The microprocessor 5 may be coupled to a local memory 7 for logging data from the motion sensor 3 and the vibration sensor 4. Thus, in a general aspect, the activity sensor may include a data logging device coupled to receive motion signals from the motion sensor 3 and mechanomyographic muscle signals from the vibration sensor 4, and store these signals as a function of time. These functions can be provided by the microprocessor and memory 7.

MMG data and motion data (e.g. from a MARG sensor) can preferably be collected simultaneously by microprocessor 5. Sampling rates may be the same or different for the two sensor types. An exemplary sampling rate from a MARG sensor suitable for gait analysis is 16 Hz. The microprocessor 5 may have multiple channels to collect data from multiple motion sensors/multiple vibration sensors at once or multiple processors may be deployed, each dedicated to one or more sensor or sensor groups. The microprocessor(s) may also receive signals from other types of sensor if required, and/or add markers in the data for other sensed events from other sensor types. Other sensed events could include, for example, physiological phenomena detected from ECG data.

In one arrangement, the microprocessor 5 and/or the memory 7 are mounted on the flexible support structure 2 as an integral part of the activity sensor 1, together with a suitable power supply. In another arrangement, the communication links 6a, 6b could comprise a short range wireless link such as Bluetooth or other near-field communication channel, and the microprocessor 5 and memory 7 could be located on a separate device. In one preferred example, the separate device could be a mobile telephone, smart phone or other personal computing device. Wired links using, for example, USB interface, are also possible.

In an alternative arrangement, the muscle vibration sensor 4 may be replaced with any other acoustic sensor, or bioacoustic sensor. In such arrangements, references to MMG signals may be replaced with corresponding references to acoustic signals. For example, other bioacoustic vibration analysis may be performed instead of muscle activity analysis. A bioacoustic sensor can collect signals indicative of foetal movements, as well as MMG signals. In a bioacoustic sensor constructed in a similar manner to the MMG sensor described above, vibration signals caused by foetal movements lead to a pressure change in the chamber when the membrane is placed on the abdomen of an expectant mother.

The activity sensor 1 has a wide range of applications of which selected ones are discussed below.

Rehabilitation

Using the activity sensor 1, a patient's activities can be continuously monitored to allow new intervention treatments. Data can be logged from both motion tracking and physiological sensing for extended periods of time. Logging muscle activity provides vital cues in relation to the health and progress of a patient in response to rehabilitation. More precise data representative of a subject's natural movement and muscle activity over extended periods of time (e.g. an entire day or even a week) has the potential to provide a generational leap in patient monitoring and lead to an entire range of new rehabilitative treatments for conditions such as stroke and neuromuscular disorders.

Applications include pre- and post-knee surgery rehabilitation monitoring, posture observation, fall detection, prosthetic control and manipulation, and general human activity analysis, predominantly in geriatrics and paediatrics. Combining muscle activity and motion data opens new horizons in anthropometrics by increasing knowledge of conditions with the addition of two different forms of biomechanical information. Motion and muscle activity give important information separately, but when synergistically combined provide better information for medical treatment and clinical intervention.

Gait/Movement/Posture Classification

Data collected over a prolonged period of time, both inertial and muscular, contains a lot of information and features that are specific to an individual subject. However, without proper analysis, these characteristics can be hard to distinguish from noise and irrelevant data. The activity sensor may therefore include a classification processor in order to analyse the collected data and extract the information and features that are specific to the subject. The classification processor is configured to receive the motion signals from the motion sensor 3 and may also receive the mechanomyographic muscle signals from the vibration sensor 4, and to classify a pattern of movement, or a posture, of at least one part of the body. Typically, this would be the part of the body to which the wearable sensor is attached, but in some circumstances it may be possible to determine movement, or a posture of, other parts of the body more remote from the wearable sensor. The classification processor may be configured to distinguish between standing, sitting, reclining and walking activities and various different postures. Thus, the classification processor may be configured to identify, from a library or database of known activity and/or posture types, one or more activities and/or postures corresponding to the received signals. The classification processor may be configured with algorithms adapted to detect signature signals indicative of predetermined activities and/or postures.

Figure 2:
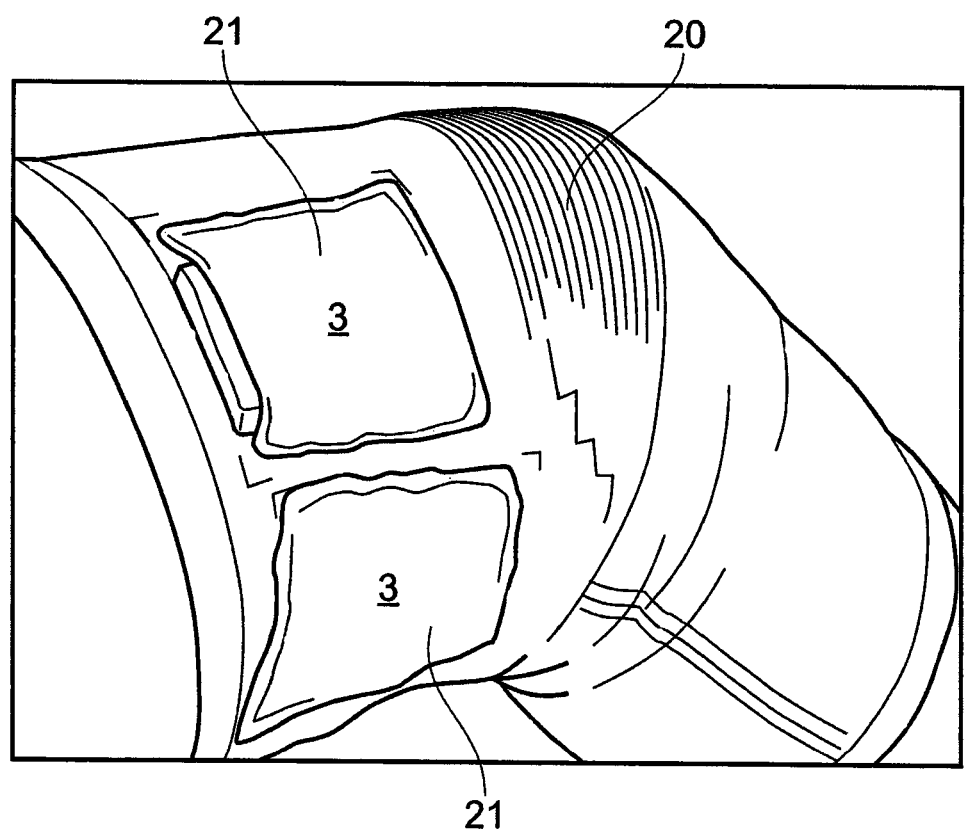
FIG. 2 shows a perspective view of a wearable activity sensor implemented in a knee brace.

In one algorithm, applied to a knee brace sensor apparatus of FIG. 2 mounted on the upper leg above the knee, sensing the direction of gravity may be used. During a standing posture, the x plane is pointing towards the ground, which gives a reading around $-1\pm0.1$ g, and the other planes (y and z) give a reading of $0\pm0.1$ g. When sitting, the y plane is now pointing towards the ground, which will give a reading of around $-1\pm0.1$ g and the other planes (x and z) read $0\pm0.1$ g. Muscular activity data can then be correlated with the particular standing posture.

The classification of walking can be detected by, for example, combining accelerometer data from each plane to determine magnitude using equation 1, where i is the current sample and n is the total number of samples; x, y and z represent the accelerations from each respective plane:

$$\text{magnitude} = \Sigma_{i=1}^{n}(x_i^2 + y_i^2 + z_i^2)^{0.5} \tag{1}$$

A threshold is determined per subject by a controlled walking task of five steps in a straight line. The data is retrieved and the threshold is determined offline by trial and error until the computed value also determines the subject to have walked five steps. Stationary states are determined to be whenever the magnitude is beneath the threshold, as per equation 2.

$$\text{stationary} = \text{magnitude} < \text{threshold} \tag{2}$$

Any period above the threshold is deemed active. Data is then split into windows of one second and the average of each window is used to determine what state the subject is in by checking the stationary periods against the averaged windows. One second windows allow each step to be recognised, as the subject's leg is stationary between strides, therefore the calculation doubles as a pedometer to determine number of steps taken. If the data window is deemed to be 'active' then the gait segment is classified as walking. However, if the data window states the subject is stationary, the calculation then determines which plane gravity is in to determine standing or sitting. In the event the subject is lying on his or her side or gravity is in a plane unrecognisable to the algorithm, the subject's state may be put into an 'other' category which can otherwise be classified differently.

Figure 4:
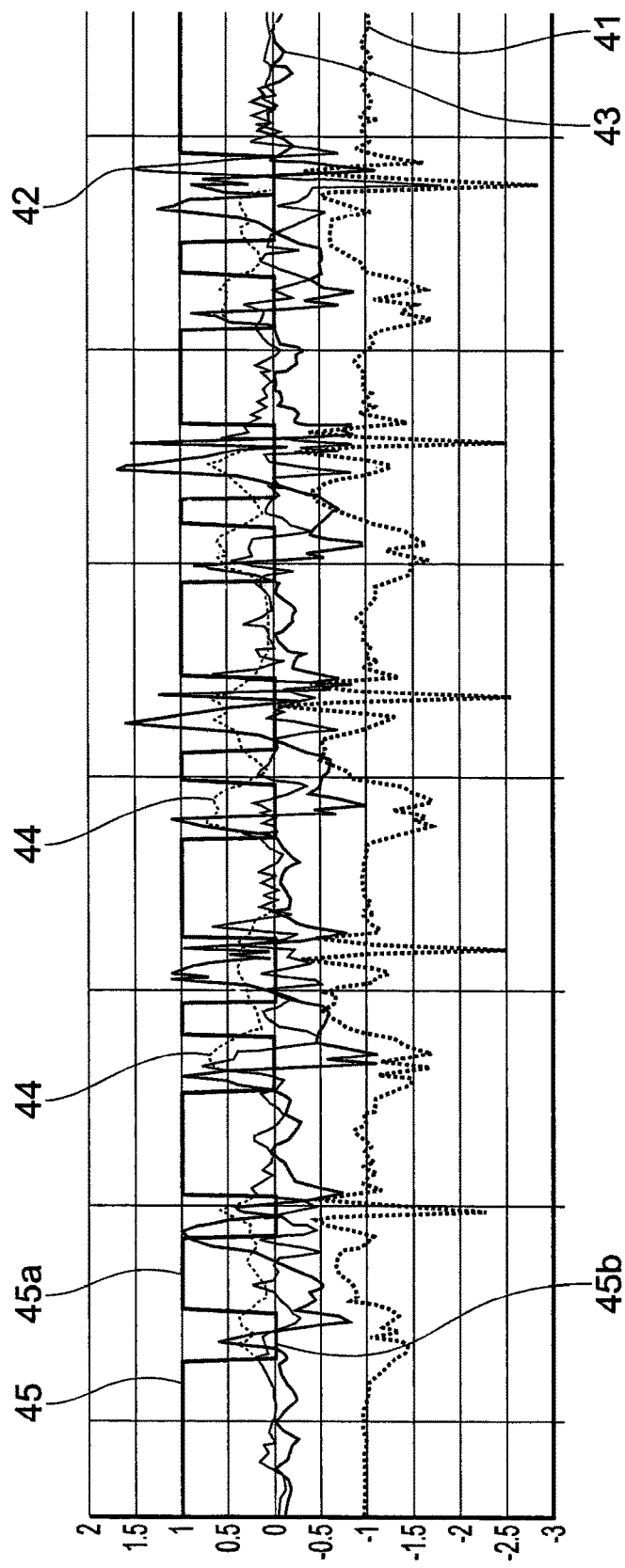
FIG. 4 shows x, y and z accelerations of a subject during a ten step walk and classification thereof.

FIG. 4 shows analysis of a ten step walk correctly determining active periods using the threshold technique described above. Solid line 41 represents x-axis acceleration, dot-dash line 42 represents y-axis acceleration, and dashed line 43 represents z-axis acceleration. The combined acceleration data corresponding to magnitude is represented by line 44. The predefined threshold has been set at 0.3 g, and a walking motion may be classified when the combined data exceeds 0.3 g. This classification is indicated by solid line 45 with the standing posture indicated at +1 (portions 45a) and walking motion indicated at 0 (portions 45b). The method was determined to be approximately 90% accurate during walking calibration tests over 15 tests.

Although the arrangement described above only requires the motion sensor data to classify a generic pattern of movement, or posture, of at least one part of the body (e.g. walking, standing, sitting), the muscle vibration sensing data may be used in conjunction therewith to further refine the classification process.

For example, the muscle vibration sensing data may be used to detect and classify other movements of the body separate or distinct from the major patterns of movement classified using the motion sensor data as further discussed below.

Thus, in a general aspect, the classification processor may be configured to use both the motion signals and mechanomyographic muscle signals to determine simultaneous patterns of movement, or postures of, multiple articulating parts of the body on which the wearable sensor apparatus is attached.

In another arrangement, the wearable activity sensor apparatus may be configured as a belt. The belt-based sensors may be configured to monitor balance, posture and key muscle activity; facilitate adoption of new movement patterns; and engage patients with direct feedback on their progress in ameliorating low back pain. The apparatus may be configured to monitor and facilitate user activation of key postural muscles associated with back dysfunction, principally lower abdominal and gluteal muscles, and activity monitors that will track balance and posture. By continuously measuring posture and providing real time biofeedback, the wearable sensor apparatus will provide the ability to facilitate active postural correction.

Figure 3:
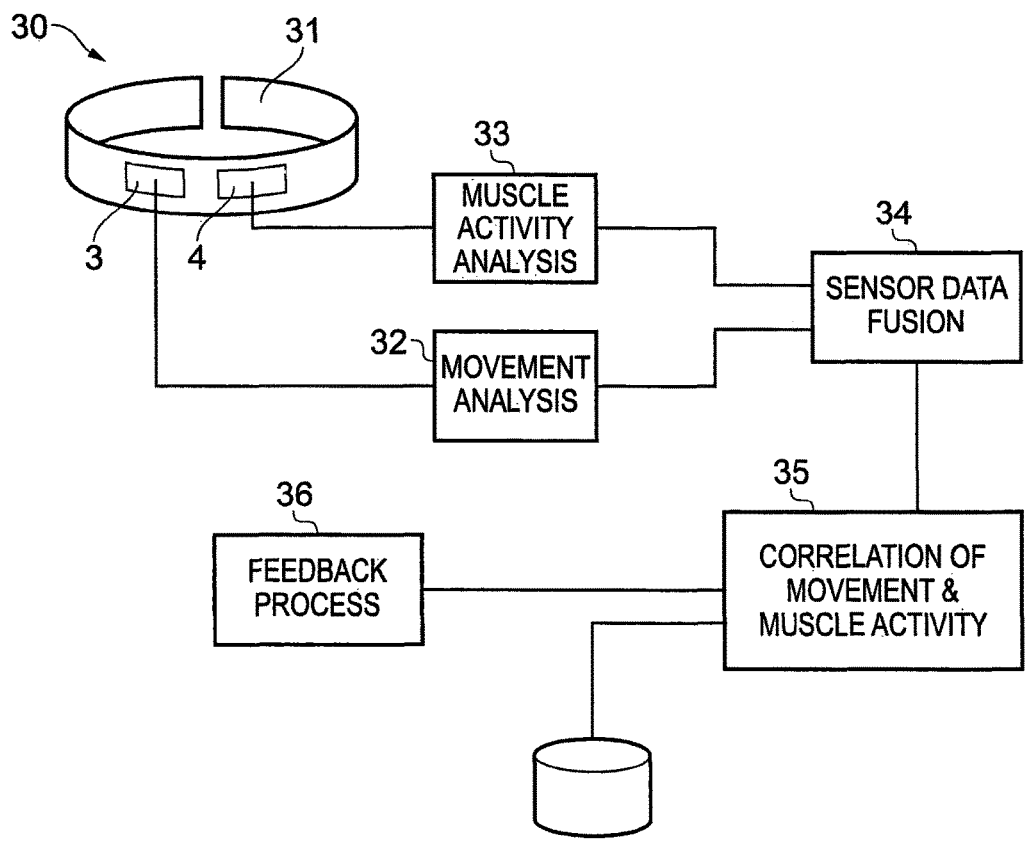
FIG. 3 shows a schematic diagram of a wearable activity sensor apparatus including signal processing and analysis processing modules.

FIG. 3 shows a schematic diagram of an activity monitoring system configured to provide analysis and feedback in relation to muscle usage correlated with subject motion.

A wearable activity sensor 30 comprises a support structure 31 in the form of a belt, which supports a motion sensor 3 and a muscle vibration sensor 4 such as previously described in connection with FIG. 1. The sensors 33, 34 are coupled to a processor including a movement analysis module 32 and a muscle activity analysis module 33. The movement analysis module 32 may be configured to perform such functions as identification of body and/or limb movements, and identification of postures, as previously described. The muscle activity analysis module 33 may be configured to identify individual muscle activities and identify muscles or muscle groups involved in sensed vibration events. The motion and muscle activity data from modules 32, 33 are combined in a sensor data fusion module 34 so that individual movement and/or posture 'events' can be aligned in time. A correlation process 35 may be configured to correlate the various movement and/or posture events with muscle activity events.

The correlated data from correlation process 35 may then be used to provide one or more possible feedback processes 36.

In one example, the feedback process 36 could be provision of a visual display of motion and related muscle activity, e.g. charted over time, for review by a clinician or the subject. The feedback process could be provision of motion and related muscle activity monitored over periods of time, e.g. successive days, to indicate whether muscle activity for predetermined postures and/or activity classifications changes over time. Such feedback process could be used to indicate an improvement, or deterioration, in activity or posture attributes over time.

In another example, the feedback process 36 could provide real time analysis directly to the subject wearing the sensor, by visual or audible feedback. For example, the processor may comprise a classification processor which classifies a pattern of movement, or a posture, of at least one part of the body of the subject, based on the motion signals, and identifies the muscular activity associated with that pattern of movement or posture, and determines whether the sensed muscular activity conforms to a predetermined pattern that is consistent with the classified pattern of movement. This predetermined pattern may represent an ideal or optimum muscular activity for a given sensed motion or posture. In the event that the sensed muscular activity does not conform to an ideal or optimum pattern of muscular activity for the sensed motion or posture, the feedback process 36 may be configured to provide a real time alert to the subject wearing the activity sensor. The real time alert may be any indication useful to assist the subject, such as a warning of poor posture or poor movement execution, an instruction to improve posture, an instruction to alter position, an instruction to engage in a specified pattern of movement or similar.

Figure 14:
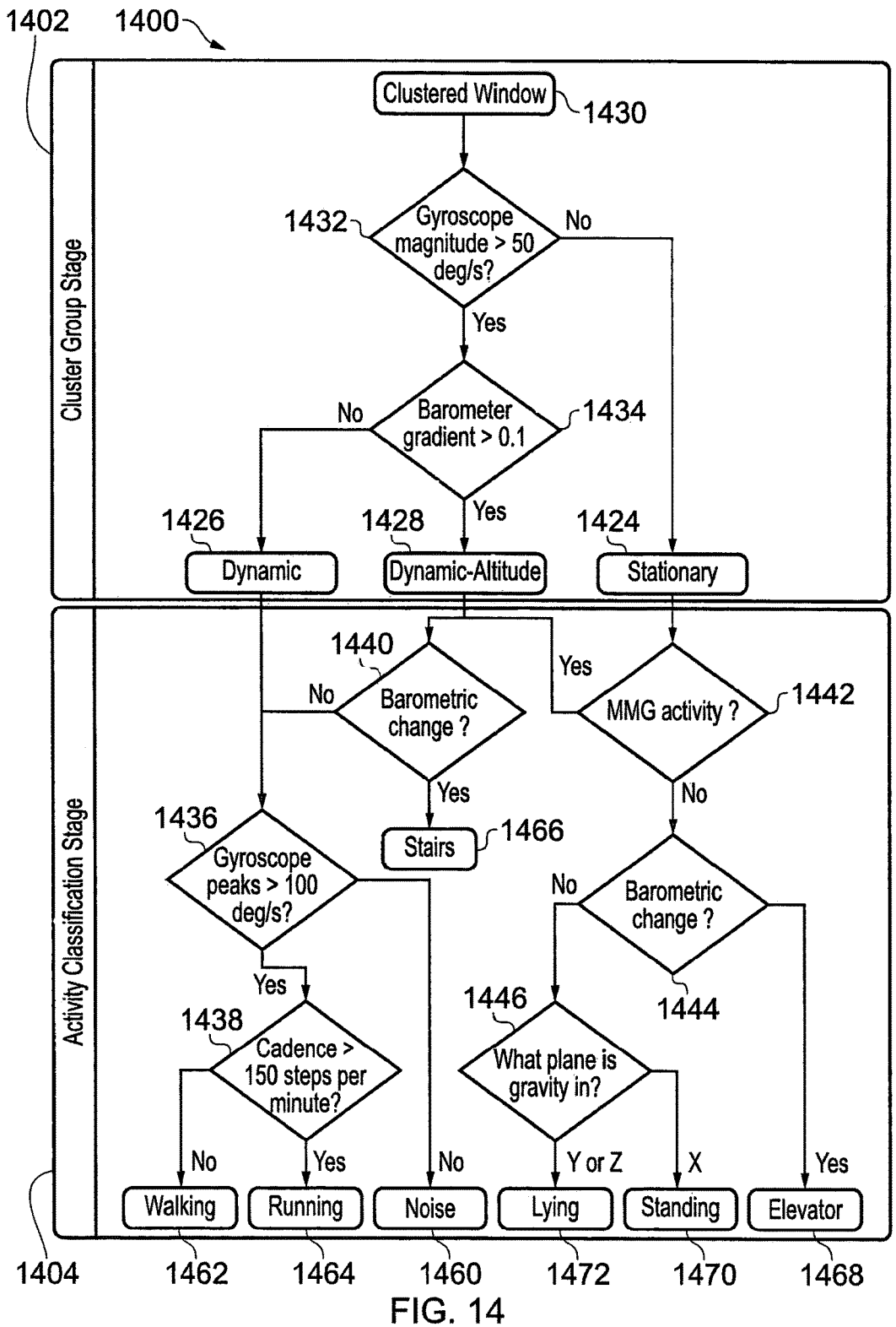
FIG. 14 shows another flow chart of a method for classifying a gait, posture or movement of a subject.

FIG. 14 illustrates a flow chart of another algorithm 1400 for classifying a gait, posture or movement of a subject. The algorithm 1400 combines motion and muscle activity in an unsupervised classification algorithm. The algorithm 1400 enables eight commonly performed activities to be identified: walking, running, ascending stairs, descending stairs, ascending in an elevator, descending in an elevator, standing, and lying down. A ninth "activity" containing noise and other unclassified activities data is also categorized.

The algorithm may be performed by a classification processor that is configured to receive:
motion signals from a motion sensor,
ambient pressure signals from a barometer; and
bioacoustic signals from a vibration sensor.

The classification processor is configured to classify, based on the received signals, a pattern of movement, or a posture of, at least one part of a body on which the sensors are attached.

The algorithm 1400 processes data in two stages 1402, 1404. In a gross group clustering stage 1402, a data or time window is split into one of three groups, each of which relates to a different class of activities; stationary activities 1424 (such as standing, lying down, and elevator), dynamic activities 1426 (such as walking, running, and noise), and dynamic-altitude activities 1428 (such as travelling on stairs). In a subsequent activity classification stage 1404, windows from each cluster group are further classified into one of nine more specific activities.

At the start of the gross group clustering stage 1402, data from each sensor type (bioacoustic and accelerometer) is windowed 1430. The window size may be selected as a number of data samples or a period of time. For example, a window size of 200 samples (four seconds of data at 50 Hz) may be used for inertial data. Such a window may be resized in order to obtain the same window size for the other sensors sampled at a different rate. For example, a four sample window may be used for a barometer operating at 1 Hz and a 4000 sample window may be used for a MMG operating at 1 kHz. It has been found that windows with a 50% overlap produce suitably good results at 50 Hz for the inertial data.

Inertial data can, optionally, be smoothed using a moving average in order to reduce the effect of transient noise on the output of the algorithm. An example moving average is:

$$ys_n = \frac{1}{2N+1}(y_{(n+N)} + y_{(n+N-1)} + \ldots + y_{(n-N)}),$$

where $ys_n$ is the smoothed value for the $n^{th}$ data point, N is the number of neighbouring data points on either side of $ys_n$, and 2N+1 is the span, such as 15 data points. Windowing 1430 can also be performed after smoothing has taken place.

Features of the windowed data are determined after the optional smoothing step. In this example, four features (mean, standard deviation, power, and covariance) are determined for each of the three axes of the accelerometer (x, y, and z) resulting in twelve parameters per window. The features can be calculated using the equations below.

$$\mu = \frac{1}{N}\sum_{n=1}^{N} y_n$$

$$\sigma = \sqrt{\frac{1}{N-1}\sum_{n=1}^{N}(y_n - \mu)^2}$$

$$\text{power} = \sum_{n=1}^{N} \frac{y_n^2}{N}$$

$$COV(a, b) = \sum_{n=1}^{N} \frac{(a_n - \mu_a)(b_n - \mu_b)}{N}$$

In the above equations, n is the current data point, N is the total number of data points in the window (200 in this example), y is the data set of one axis, μ is the mean, σ is the standard deviation, and a and b each correspond to one of the three accelerometer axes (x, y, or z). COV represents a covalent matrix:

$$COV = \begin{bmatrix} x,x & x,y & x,z \\ y,x & x,y & y,z \\ z,x & z,y & z,z \end{bmatrix}$$

Values in the diagonal of the covariance matrix where the covariance of an axis is applied against itself result in the variance of that axis, and may therefore be ignored. Likewise, values below the diagonal are mirror values of that above the diagonal and are also ignored.

A K-means clustering algorithm using a squared Euclidean distance method may be used to cluster windowed data into one of three clusters based on the parameter matrix created from the four features above. The objective function of the K-means algorithm is:

$$J = \sum_{n=1}^{N} \sum_{k=1}^{K} r_{nk} \| y_n - c_k \|^2,$$

where again y, n and k are the dataset, current data point and current cluster respectively. N is the total number of data points in the dataset. K is the number of cluster groups (three in this example, which relate to dynamic activities 1426, dynamic-altitude activities 1428 and stationary activities 1424). $c_k$ is a centroid of the current cluster, and $r_{nk}$ is a binary indicator variable (where $r_{nk}$ is equal to one if a data point belongs to cluster k, otherwise zero).

In order to predict data points belonging to one of the three cluster groups the values of $r_{nk}$ and $c_k$ have to be found in order to minimise J. Initial values of $c_k$ may be randomly determined. A two stage process of calculating $r_{nk}$ and $c_k$ can then be repeated until results converge. A process for achieving convergence is summarised below.

1) Centroids of the clusters are initialised with random values.
2) Each data point is attributed to the closest cluster using:

$$r_{nk} = \begin{cases} 1 & \text{if } k = \operatorname{argmin}_j \| y_n - c_j \|^2 \\ 0 & \text{otherwise} \end{cases}$$

3) The position of each cluster is re-evaluated so that it corresponds with the mean of all data points belonging to that cluster using:

$$c_k = \frac{\sum_n r_{nk} y_n}{\sum_n r_{nk}}$$

4) Steps 2 and 3 are repeated until results converge.

As different initial cluster centroids can produce slightly differing results, the steps above may be repeated a number of times, such a five times, using different sets of initial cluster centroid positions in order to provide more accurate results.

The steps above are performed for each window. With each window now placed within one of three cluster groups it is still unknown which particular class of activity (dynamic activities 1426, dynamic-altitude activities 1428 and stationary activities 1424) the subject was performing in that window. That is, it is unknown which of the three groups relates to the stationary, dynamic, or dynamic-altitude activities. An a priori approach is used to segregate each window into a known activity by assuming certain characteristics of each activity and which cluster groups relate to it.

A gyroscopic magnitude and barometer gradient are determined for each window. An average of these parameters is calculated for each cluster group, which is then used to label which of the three groups of clusters belongs to the stationary, dynamic, or dynamic-altitude groups.

The stationary group 1424 is defined by determining 1432 that an average gyroscopic magnitude for one of the groups is below a first threshold rate, such as 50°/s.

The dynamic group 1426 is defined by determining 1432 that the average gyroscopic magnitude for one of the groups is above the first threshold rate and by determining 1434 that an average barometer gradient for that group is below a pressure threshold gradient, such as 0.1 meters.

The dynamic-altitude group 1428 is defined by determining 1432 that the average gyroscopic magnitude for one of the groups is above the first threshold rate and by determining 1434 that the average barometer gradient for that group is above the pressure threshold gradient.

For the dynamic group 1426, it is determined 1436 whether a peak gyroscopic magnitude for a cluster in that group is above a second threshold rate, such as 100°/s. If the gyroscopic magnitude for that cluster is not above the second threshold rate then the activity of the cluster is categorised as "noise" 1460. If the gyroscopic magnitude for that cluster is above the second threshold rate then it is determined 1438 whether the cadence of the subject is greater than a cadence threshold, such as 150 steps per minute. If the cadence of the subject is not greater than a cadence threshold then the activity of the cluster is categorised as "walking" 1462. If the cadence of the subject is greater than a cadence threshold then the activity of the cluster is categorised as "running" 1464.

For the dynamic-altitude group 1428, it is determined 1440 whether a barometric change has occurred for a cluster in that group. If a barometric change has occurred then the activity of the cluster is categorised as "stairs" 1466. An increase in pressure is indicative of a decrease in altitude (going down in the lift/stairs), whereas a decrease in pressure is indicative of an increase in altitude. If a barometric change has not occurred then it is determined 1436 whether the peak gyroscopic magnitude for that cluster is above the second threshold rate and the cluster is treated as described above for the dynamic group 1426.

For the stationary group 1424, it is determined 1442 whether MMG activity has occurred for a cluster in that group. If MMG activity has occurred then it is determined 1440 whether a barometric change has occurred for that cluster, and that cluster is subsequently treated as described above for the dynamic-altitude group 1428. If MMG activity has not occurred then it is also determined 1444 whether a barometric change has occurred for that cluster. However, in this case:

if a barometric change has occurred then the activity of the cluster is categorised as "elevator" 1468; or if a barometric change has not occurred then it is determined 1446 in what plane of gravity the device lies. In this example, if the device lies in a Y or Z plane then the activity of the cluster is categorised as "lying" 1470, and if the device lies in an X plane then the activity of the cluster is categorised as "standing" 1472.

The table below shows a breakdown of average detection accuracy over two trials of the algorithm 1400. The trial contained six subjects performing various activities. Accuracy was determined by validating each determined window activity against the actual activity of the subject during that window. A percentage was calculated from number of correct windows divided by total number of windows in each trial. The overall accuracy, by taking the mean of accuracy across all subjects and trials, is found to be 97%.

| Subject | Activities | Missing Group | Accuracy (%) |
| --- | --- | --- | --- |
| 1 | S, W, SD, LU | None | 97.60 |
| 2 | S, W, SU, LD | None | 96.30 |
| 3 | S, W, SU, SD | None | 97.46 |
| 4 | S, W, LU | Dynamic-Altitude | 98.06 |
| 5 | S, W, R | Dynamic-Altitude | 95.16 |
| 6 | S, L | Dynamic, Dynamic-Altitude | 100.00 |

S = standing, L = lying, W = walking, R = running, SD = stairs down, SU = stairs up, LD = lift down, LU = lift up.

The algorithm 1400 can be applied without the requirement to perform control experiments or pre-collection data labelling and can be used in an unsupervised environment. In contrast, methods which use supervised classification require additional trials of each known activity. In applications where gait or muscle activity changes are expected over time, such as physiotherapy or gait retraining, the trials experiments for supervised classification need to be re-determined before each usage session, making such methods inconvenient for practical use. The use of an unsupervised classification therefore can provide improved accuracy in classifying undirected human activity.

Foetal Movement and Health Monitoring

Another application for the wearable sensor apparatus is in the field of foetal monitoring.

Foetal movement is generally quantified using ultrasound or MRI scanning, both of which are expensive and must be undertaken in a clinical setting. Furthermore, there is no way to reliably monitor foetal movements outside the time window when a patient is scanned in a clinical environment. Maternally-sensed decreased foetal movements are a common reason for consultation with obstetric services, but maternal perception of foetal movement is highly subjective and patient-dependent. Incorrectly perceived decreased foetal movements can lead to high anxiety in an already anxious patient group.

A wearable activity sensor such as described above may also be adapted to extended or long term foetal monitoring. The motion sensor and the vibration sensor may be incorporated into sensors incorporated into, for example, a lumbar support belt or a maternity support band. A particular problem with foetal monitoring can be separating signals corresponding to maternal movement with those corresponding to foetal movement.

In one example, the sensor may include a classification processor configured to receive motion signals from the motion sensor 3 and to receive acoustic signals or mechanomyographic muscle signals from the vibration sensor 4, and to determine when the signals correspond to foetal movement.

In one preferred arrangement, a signal processing algorithm identifies movement and/or muscle signals that can be attributed to maternal activity and separates these from the input signals to determine signals attributable to activity of the foetus. The frequency and intensity of foetal movements in a given time period may be monitored to ensure well-being of the foetus. Preferably, the foetal movement signals may comprise acoustic signals received by an acoustic vibration sensor. The data may be logged and periodically downloaded, or continuously assessed and an alarm triggered if there is a period of inactivity or reduced activity exceeding a threshold.

In one arrangement, the motion signals from the motion sensor may be used to detect maternal activity as a function of time, including movement and posture such as standing, sitting, walking, breathing and heartbeat. The periods of maternal activity can then be used to isolate time periods when acoustic vibration signals corresponding to foetal movement may be tracked without occlusion from maternal activity. After removal of the maternal motion data, the remaining acoustic sensor data can be used to detect foetal movement in utero. The foetal acoustic sensor data may comprise acoustic signatures that can be matched to predetermined templates indicative of foetal activity.

Other signal processing algorithms may be considered to separate interfering signals related to maternal activity from the signals captured by the acoustic sensor, thereby isolating the foetal acoustic signals indicative of foetal movement.

Other sensor types may be added to the apparatus for enhanced monitoring.

Figure 11:
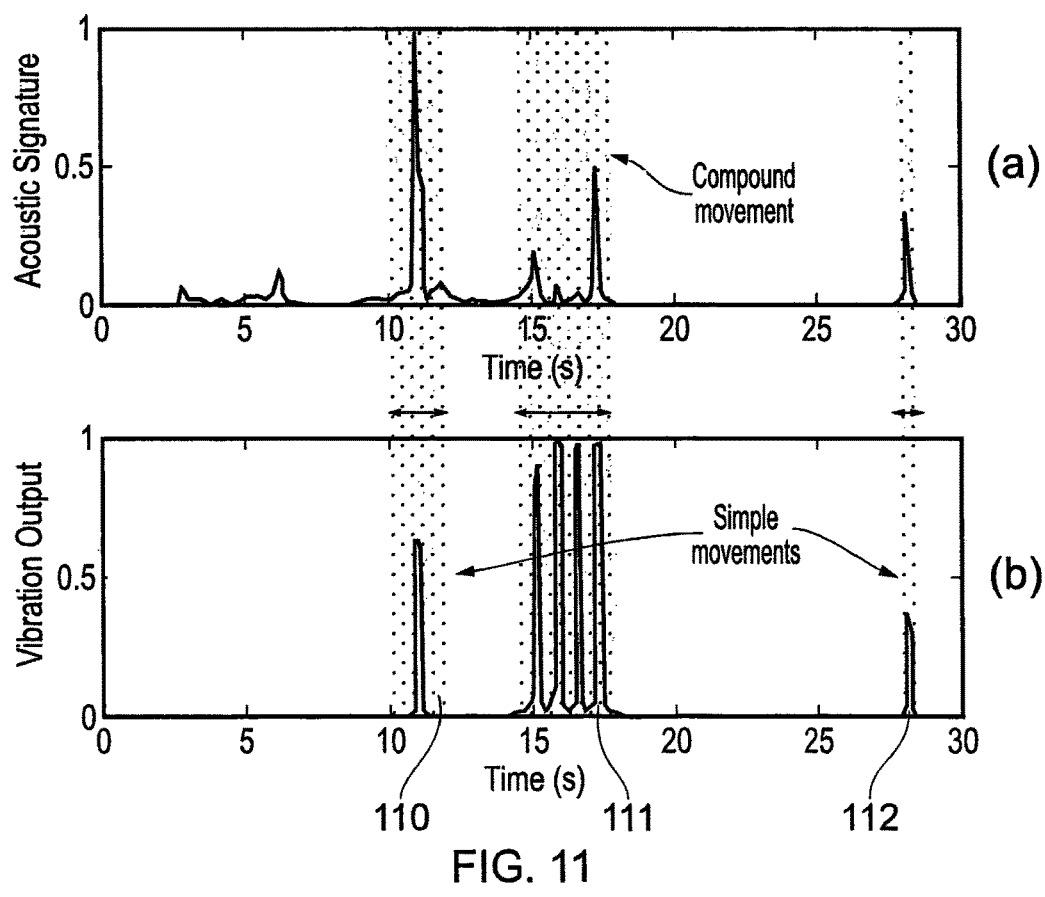
FIG. 11 shows (a) acoustic sensor output, and (b) a gel-based vibration sensor output corresponding to foetal movement in a pregnant subject.

FIG. 11 illustrates acoustic signal output for a system monitoring acoustic output from a subject experiencing foetal movements. The apparatus used comprised two inexpensive bioacoustic sensors and an inertial measurement unit (IMU), together with an additional sensor for validation, incorporated into a back support belt. The additional sensor was an expensive electro-active polymer gel sensor capable of detecting low frequency vibrations such as abdominal vibrations associated with foetal movements. The subject was at rest at the time of the experiments to minimise maternal movement artefacts. The data from the sensors was smoothed and signal energy plotted. Processed data from the gel sensor is shown as 'Vibration Output' in FIG. 11b. Highlighted windows 110, 111, 112 show a number of simple and compound foetal movements taken from the gel sensor output (classified as two simple movements 110, 112 and one compound movement 111) within a 30 second window. This output was used as a baseline to compare with a bioacoustic sensor to test its capacity to capture the same movements. The output of that sensor, processed in the same way, is shown in the 'Acoustic Signature' of FIG. 11a. The results show that the same simple and compound movements were captured by the inexpensive bioacoustics sensor. Simple and compound foetal movements corresponding to maternal assessment can thus be captured with the bioacoustics sensor, and the sensor output can be processed to recognize these movements. The IMU can be used to determine maternal activity enabling isolation of foetal activity as discussed above, and below with reference to FIGS. 16 and 17.

Foetal movement can be localised in the uterus by means of several bioacoustic sensors positioned across the expecting mother's abdomen. Higher signal magnitudes seen on individual bioacoustics sensors can provide a sense of foetal position in the womb.

Figure 12:
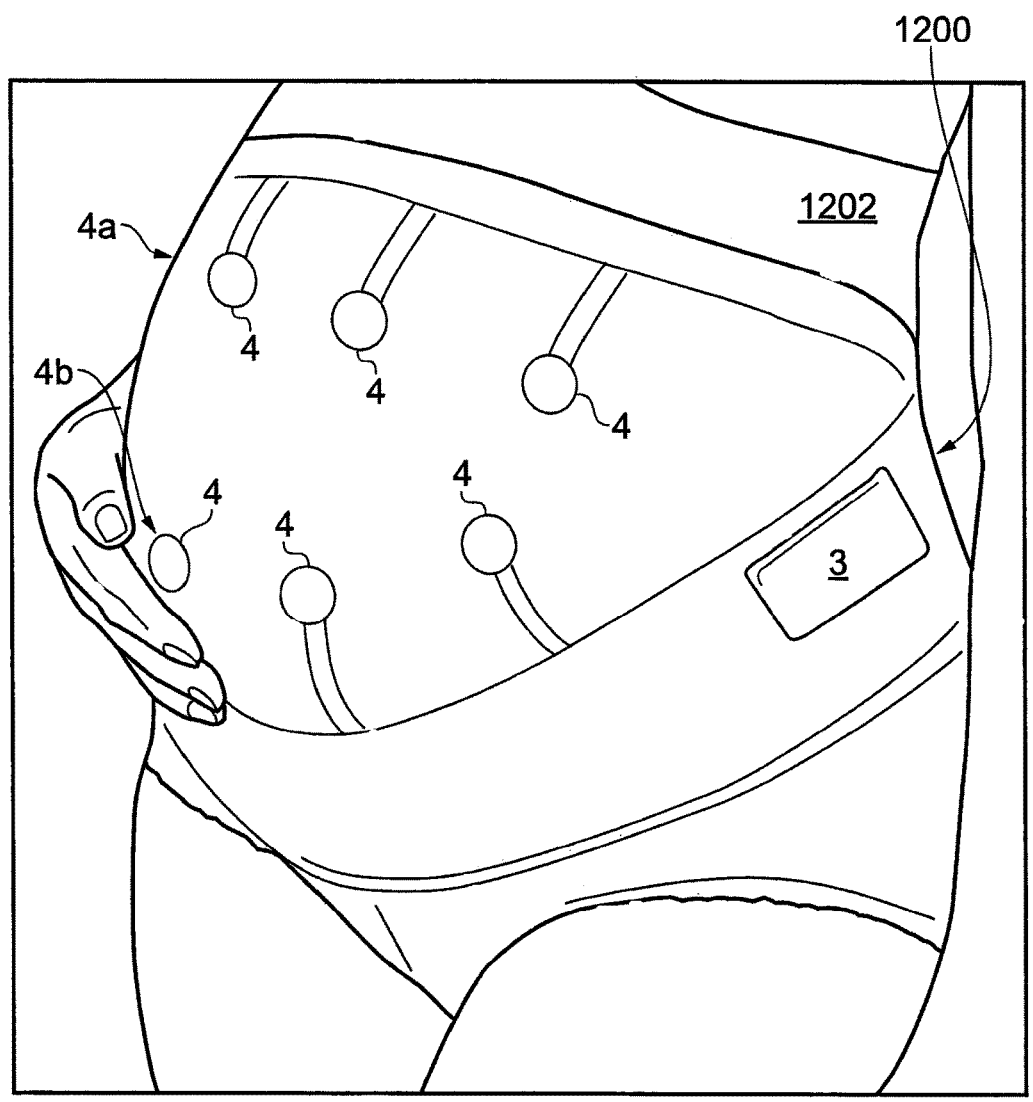
FIG. 12 shows a wearable activity monitor for detecting foetal movements.
Figure 15:
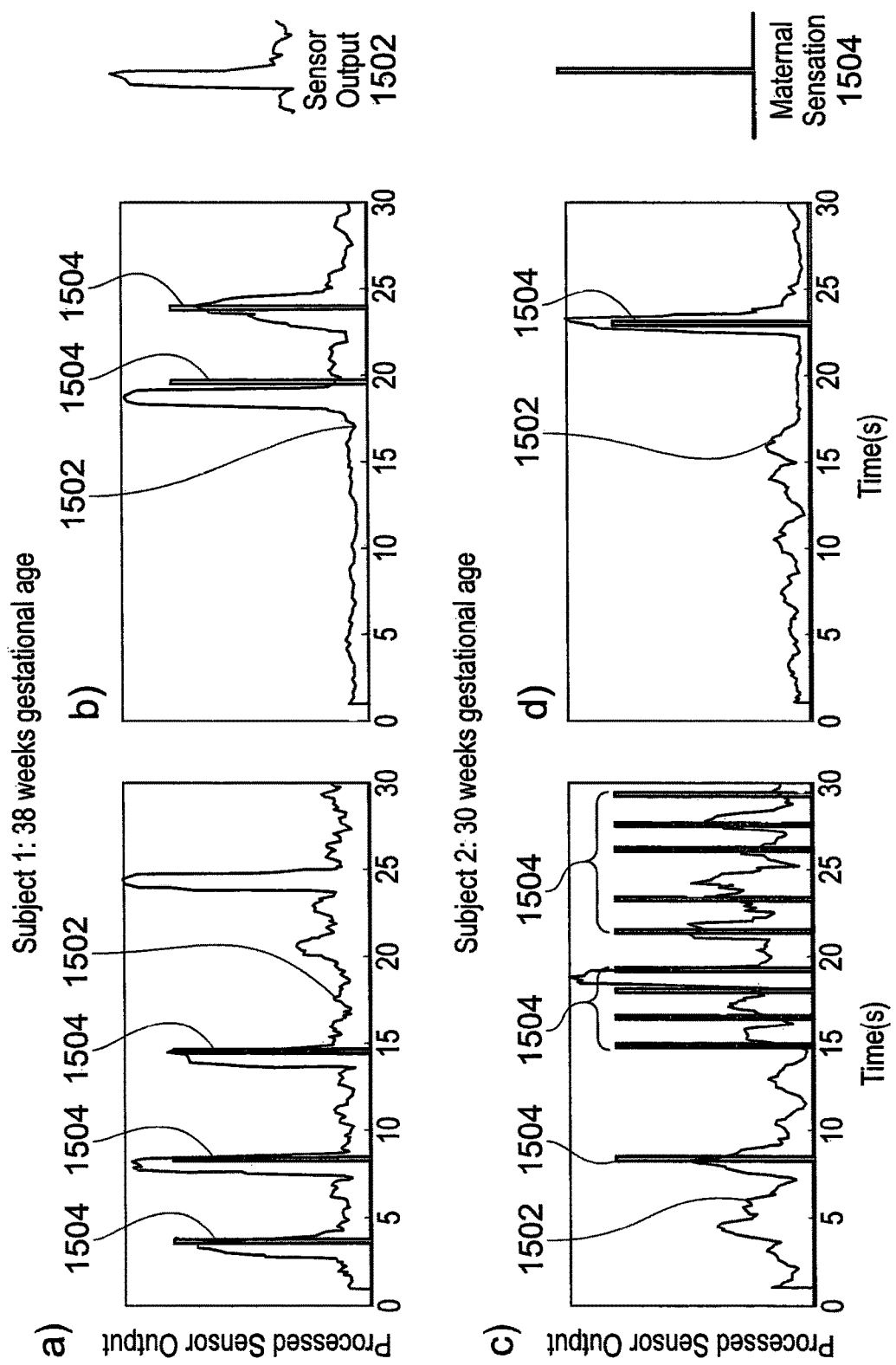
FIG. 15 shows acoustic sensor output and maternal sensation data corresponding to foetal movement in pregnant subjects.

FIG. 12 illustrates a maternity support structure 1200, which is an example of a support for a wearable activity sensor apparatus such as that described with reference to FIG. 1 and may provide the bioacoustic data illustrated in FIG. 11, above, or FIG. 15, below. The support structure 1200 comprises an inertial sensing unit 3 and six bioacoustic sensors 4. The bioacoustic sensors 4 are presented in two rows 4a, 4b and are presented against the skin of a subject 1202 on the inner surface of the support structure 1200. The bioacoustic sensors 4 are configured to sense acoustic vibrations and the inertial sensing unit 3 is configured to sense two or three dimensional movement and an orientation of the sensor 4.

Each of the bioacoustic sensors 4 preferably provides a volumetric chamber with a membrane stretched over an opening in a housing of the chamber. A difference in volume of the volumetric chamber whenever the membrane is deformed by bioacoustic vibration is detected using a microphone. When the bioacoustic sensors 4 are placed on the abdomen of an expectant mother, vibration signals caused by foetal movements lead to a pressure change in the respective chambers of the bioacoustic sensors 4. In some examples, the location and strength of the foetal movements may be used to determine foetal orientation in the womb. For example, the apparatus 1200 may be used to identify foetuses in a foetal breech position.

Figure 13:
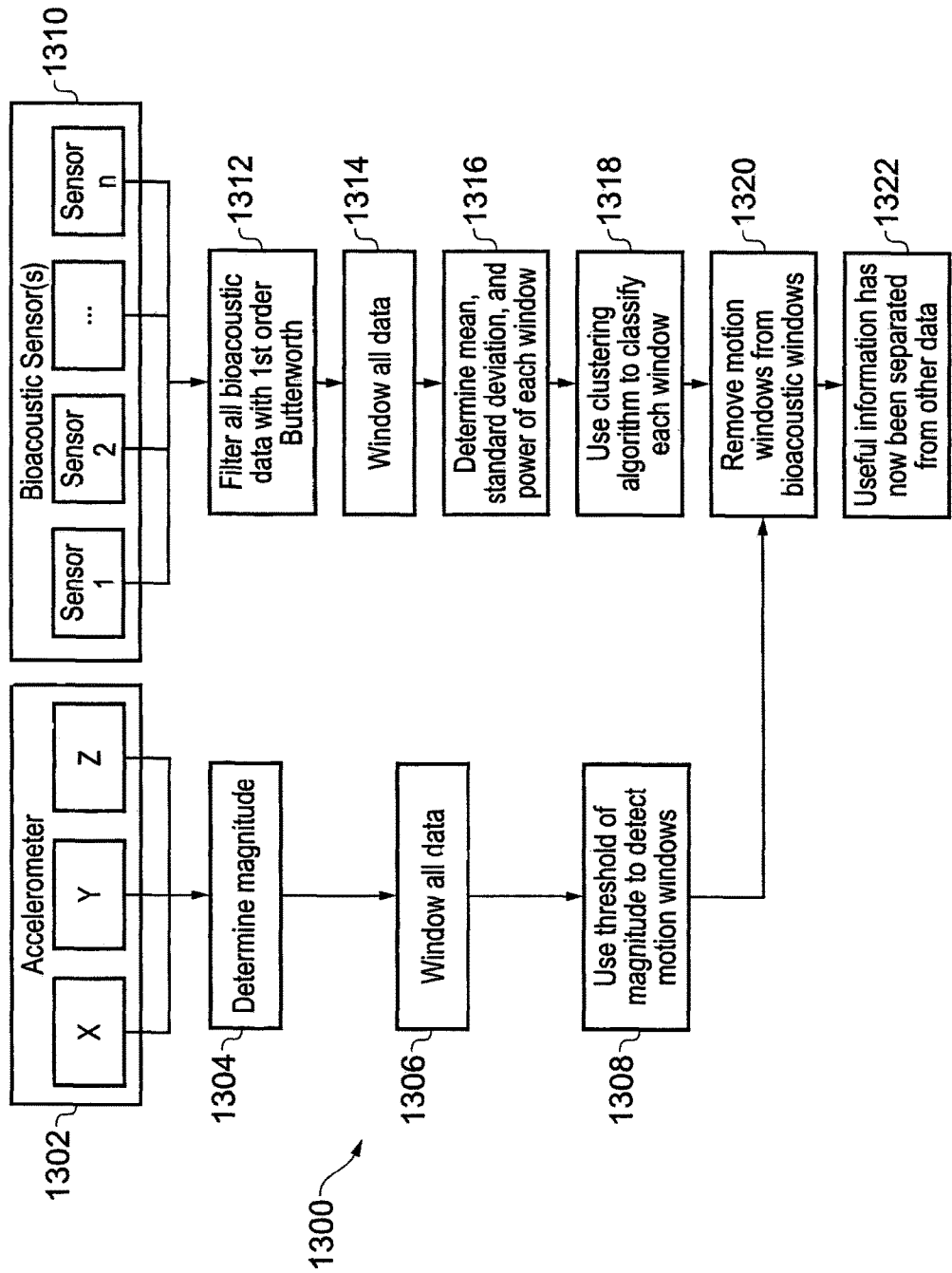
FIG. 13 shows a flow chart of a method for classifying a subject's movement, including foetal movement within the subject.

FIG. 13 illustrates a flow chart of a method 1300 for classifying a subject's movement (including the movement of a foetus) by collecting and combining information from a three dimensional accelerometer and bioacoustic sensors.

Three dimensional movement and orientation signals are provided 1302 by an accelerometer. A magnitude of an acceleration detected by the accelerometer is determined 1304. The magnitude may be determined 1304 using, for example, equation (1) discussed previously. The accelerometer data is then windowed 1306 and thresholding is used to detect motion of the windowed data 1308 using, for example, equation (2) discussed previously. A window of data may be a discrete number of samples of data, or the samples taken within an interval of time.

One or more bioacoustic sensors provide 1310 acoustic vibration data in parallel with the acquisition of data by the accelerometer. The acoustic vibration data is passed through a filter 1312, such as a first order Butterworth filter. The filtered vibration data is windowed 1314 and features of the windowed data are determined 1316. Four features (mean, standard deviation, power, and covariance) are determined 1316 for each of the three axes of the accelerometer (x, y, and z) resulting in twelve parameters per window. The extraction of features from windowed data is described in detail in relation to FIG. 14 and similar techniques can be used in the determination 1316 in the present algorithm 1300.

A cluster algorithm 1318 is used to classify each window. For example, a K-means clustering algorithm using a squared Euclidean distance method may be used to cluster windowed data into one group of clusters based on a parameter matrix created from the four features above. The value of a cluster is indicative of the type of activity that is being performed by the subject during the window associated with that cluster. The use of a cluster algorithm has been found to provide an adaptable and robust method of classifying data and so may be advantageous compared to other methods of classifying observed data using pre-existing profiles. Cluster analysis is also discussed in further detail with reference to the example of the method of FIG. 14.

At a combining step 1320, the windows of accelerometer data in which motion has been detected are used to determine which windows of bioacoustic data relate to bioacoustic activity within the subject and which windows relate to noise signals. At this stage, useful information has been separated 1322 from other data by the combination of motion sensor data and acoustic vibration data. The use of inertial data in cancelling vibration artefact is described further below with reference to FIGS. 16 and 17.

FIGS. 15a to 15d illustrate acoustic, or bioacoustic, signal output for a system monitoring acoustic output from two pregnant subjects experiencing foetal movements. The apparatus used to collect this data comprised three inexpensive bioacoustic sensors, an inertial measurement unit (IMU), and a button for the pregnant subject to press when she felt a foetal movement. The apparatus was incorporated into a back support belt.

The data from the bioacoustic sensors may be processed using a method similar to that described with reference to FIG. 13. For example, the data from the bioacoustic sensors may be i) smoothed, ii) filtered using a $1^{st}$ order Butterworth filter, and iii) split into even sized windows across a data set. Motion may be determined by thresholding accelerations within the inertial data. Motion artefacts may be removed from the bioacoustic data to reduce false positives. An example of the signal processing steps of vibration artefact removal is discussed in detail below with respect to FIGS. 16 and 17. Features from each bioacoustic sensor window are determined, including mean, standard deviation, and power of the signal. These features are then processed through a clustering algorithm in order to classify the activity associated with each window. Examples of classification states include: noise, foetal activity, and stationary data.

FIGS. 15a and 15b illustrate a correlation between bioacoustic sensor output 1502 and maternally sensed foetal movements 1504 recorded by the pregnant subjects using the push buttons. The bioacoustic sensor output 1502 correlates with movements perceived by the mother, and can also detect foetal movements not detected by mother (as seen in FIG. 15a), and foetal hiccups (FIG. 15c, verified by mother). The system was able to isolate maternal movements, segment data from real-world activity, and extract foetal movement signatures. The results show that foetal movements corresponding to maternal assessment can thus be captured with the bioacoustic sensor, and the sensor output can be processed to recognize these movements.

The acoustic sensor output may also be used to derive a heart rate signal or breathing signal representative of the heart rate or breathing of either or both the maternal or foetal subject.

FIGS. 16a and 16b illustrate, as function of time, gyroscope (GYR X, Y, Z) and corresponding muscle (EMG, MMG) response data 1604-1608 for a subject during a walking task.

Bioacoustic data, such as MMG data, collected using a microphone can be susceptible to motion and skin artefacts and oscillation noise caused during heel strike and toe off. The oscillation noise due to impact vibration can be filtered from the MMG data using IMU data as a guide to where impacts occurred. In this way, the IMU can be used to determine maternal activity enabling isolation of foetal activity, for example.

Figure 16:
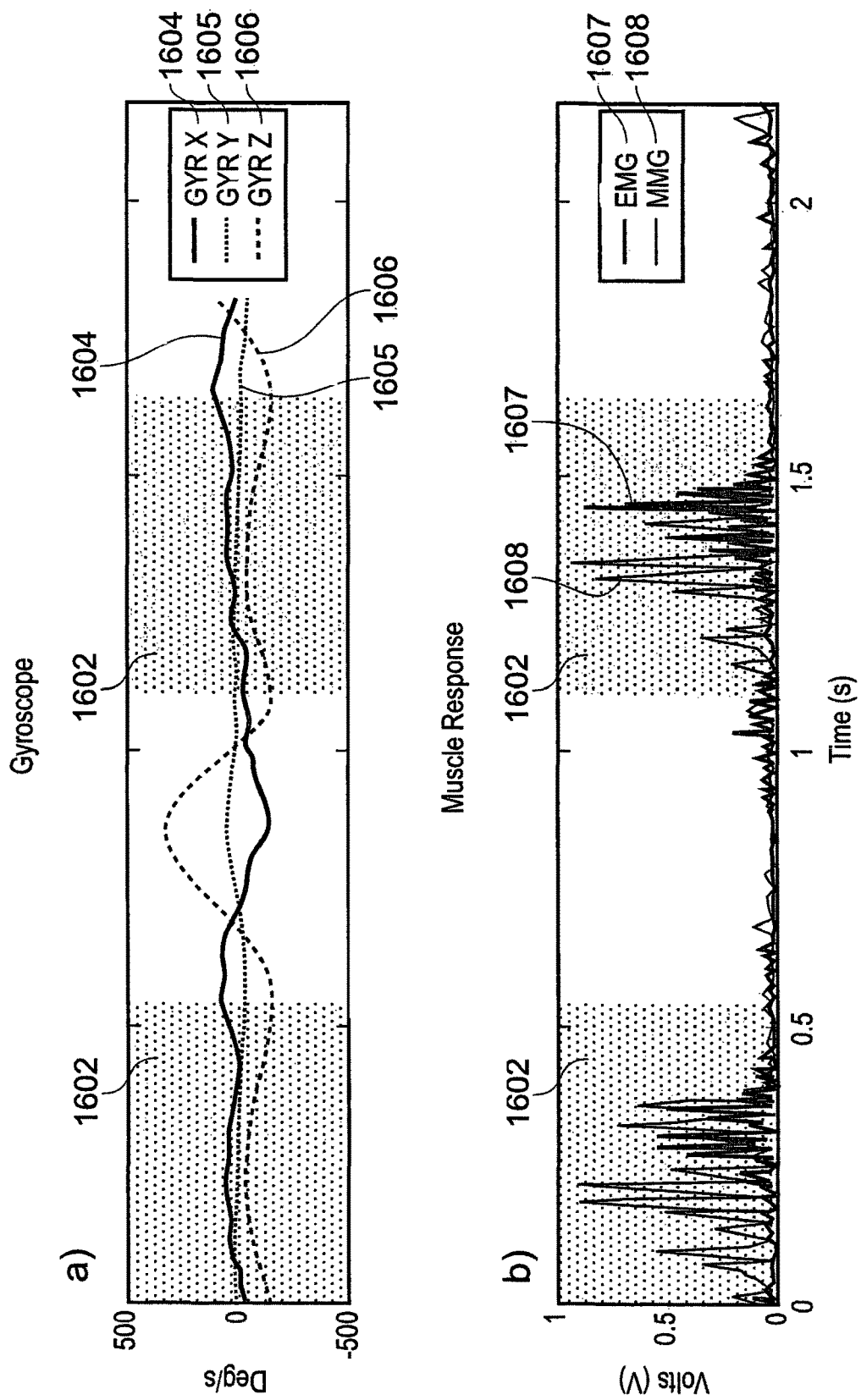
FIG. 16 shows (a) gyroscope and (b) corresponding muscle response data for a subject during a walking task.
Figure 17:
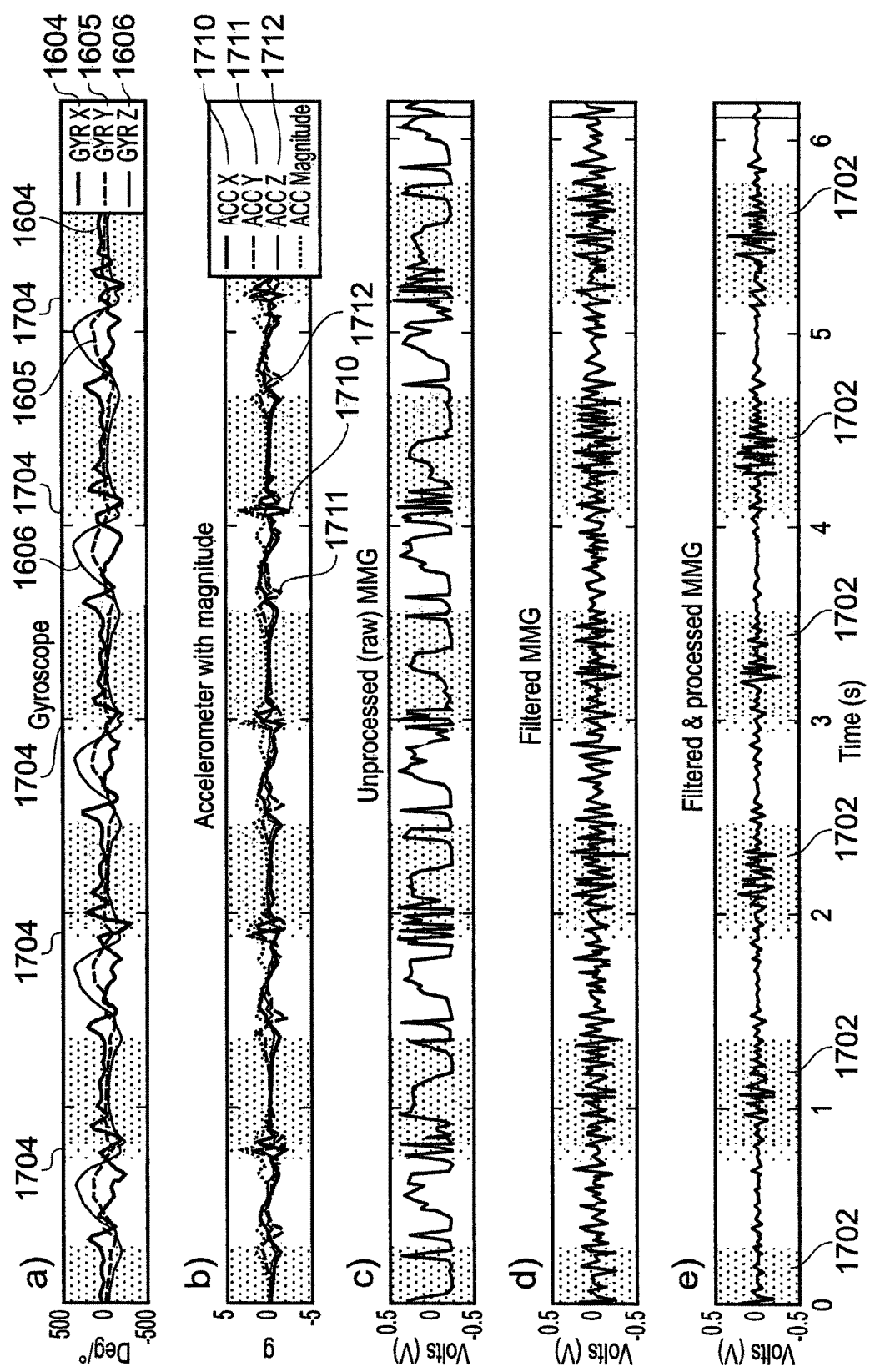
FIG. 17 illustrates (a) gyroscopic data, (b) accelerometer data with calculated magnitude, (c) unprocessed (raw) MMG data, (d) filtered MMG data, and (e) filtered and processed MMG for a subject during a walking task.

Flat foot periods 1602 during the subject's gait are shaded. The observed MMG responses shown in FIG. 16 are at their highest here during these periods 1602, as is an EMG response profile shown for comparison. There is little MMG signal during the flat foot portion of the stance.

In one example, accelerometer data is normalised between one and zero and resampled at a frequency, such as 1 kHz, to match a sampling rate for the MMG. The MMG data is then filtered using a band-pass Butterworth filter between 10 Hz and 150 Hz. The filtered signal is then divided by the accelerometer magnitude. Therefore, the observed vibration signal can be significantly reduced at times when impact events occur in order to compensate for the vibrations caused by these impact events. This method of noise reduction is useful because very little muscle contraction is expected at the impact points during a subject's gait and so the reduction in sensitivity at these points may be acceptable for some sensing applications. When measured accelerations are small, the MMG activity tends to change only marginally. Instead, the majority of muscular activity from the gastrocnemius is produced during plantar flexion of the ankle, thus a signal response is expected during the flat foot stance period of the gait cycle before toe off.

FIGS. 17a to 17e illustrate as a function of time: gyroscopic data (GYR X, Y, Z) 1604-1606 in FIG. 17a; accelerometer data (ACC X, Y, Z) 1710, 1711, 1712 with calculated magnitude (ACC Magnitude) as a dashed line in FIG. 17b; unprocessed (raw) MMG data in FIG. 17c; filtered MMG data in FIG. 17d; and filtered and processed MMG in FIG. 17e.

Flat foot periods 1702 during the subject's gait are shaded. A comparison between the gyroscope data of FIG. 17a and the processed MMG of FIG. 17e show that the flat foot stages of gait, highlighted with a blue background, coincide with muscular contraction periods.

Heel strike periods 1704 are also labelled in FIGS. 17a to 17e. These heel strikes provide vibration artefacts. The unprocessed (raw) MMG and filtered MMG profiles in FIG. 17c and FIG. 17d include artefacts due to the heel strikes. The processed MMG data has been filtered, smoothed, and motion and corrected for vibration artefacts by dividing the filtered MMG of FIG. 17d by the accelerometer magnitude of FIG. 17b.

Real Time Biomechanical Activity Tracking

Stick figure tracking has been performed using two MARG sensors on each segment of a limb, and results displayed in real-time. The data may be transmitted via Bluetooth to a computer where it displays the subject's movement in a 3D stick figure. A sampling rate of 16 Hz for each MARG sensor was used.

Simultaneous monitoring of acoustic or MMG sensor data enables more detailed information of the subject's motion, including isometric muscular action and isokinetic muscular action. Both isometric and isokinetic movements can be tracked and displayed in real time. The use of acoustic (e.g. microphone sensed) data provides accurate dynamic data as well as static, as it is unhindered by motion noise produced by isokinetic movements. The use of microphone sensed MMG data is preferred as it tends to be relatively uncontaminated by body motion that might be detected by using accelerometer-based MMG data sensing, which may be difficult to filter out without compromising low frequency MMG signals and possibly high frequency harmonics. However, in other arrangements, both microphone-based and accelerometer-based MMG sensing could be deployed.

Real time motion tracking has many uses, such as providing output control signals to motive apparatus such as robotic systems, where control of the movement of the motive apparatus or robotic system is provided by, for example, emulation of movements (e.g. arm, head or trunk movements and/or gestures) of the controlling person. Motion sensors alone may not be adequate or optimal to capture the entire range of movements commonly used (e.g. arm, wrist, and finger action) to control devices such as joysticks or computer mice or other interfaces for robotic control. The fusion of inertial sensors capturing gross (e.g. arm) movements and robust acoustic sensors tracing physiological activity associated with finer (finger) movements, provides a novel approach to controlling external peripheral devices such as computers, remote robotic mechanisms, or prosthetic/assistive devices. The activity sensing apparatus described above is configurable to include an interface module to provide output control signals for such a motive apparatus based on movements detected by the classification processor. The output control signals may be provided to, for example, a prosthesis or robotic device.

Figure 5:
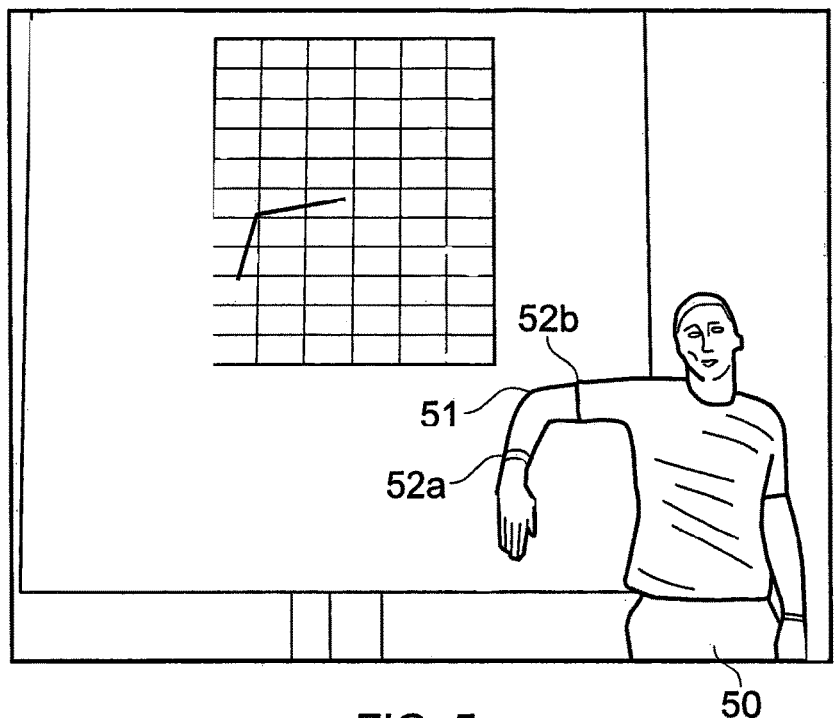
FIG. 5 shows a subject wearing two activity sensors deployed on upper arm and forearm with real time feedback display.
Figure 6:
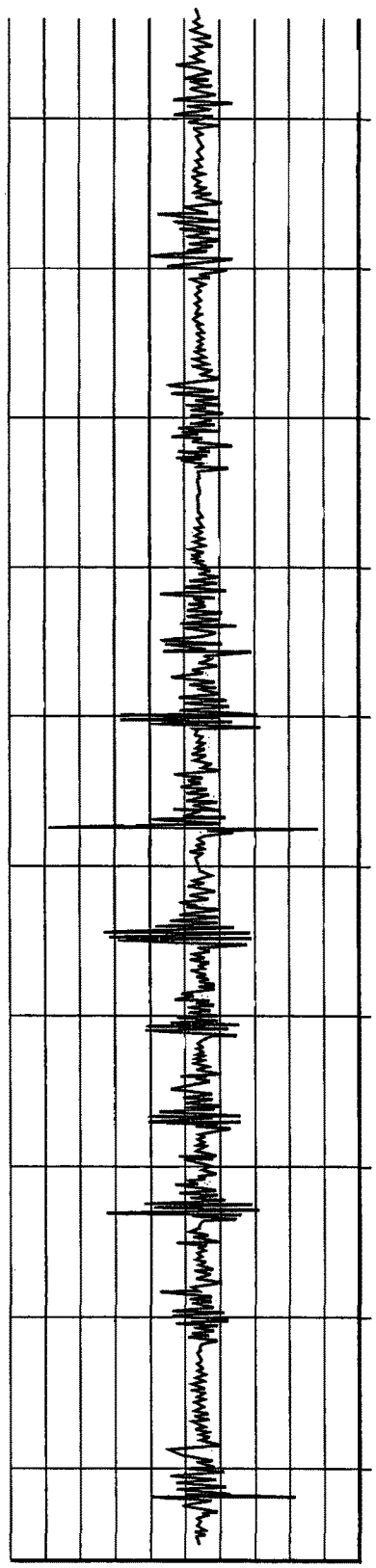
FIG. 6 shows a graph of mechanomyography (MMG) data obtained during isometric contraction of the forearm with fist clenches.

In an example where sensors are disposed on a subject's upper arm and forearm, the motion sensor data may be used to track a subject's arm movements to a high degree of speed and accuracy, with 16 Hz sampling rate for each MARG motion sensor being sufficient enough to follow quick gestures of two segments of a limb. FIG. 5 shows a subject 50 displaying movement of both segments of an arm 51 using two such wearable sensors 52a, 52b. MMG sensor data as shown in FIG. 6 enables correct detection of minute muscle activity in a subject's flexor carpi radialis muscle while performing an isometric contraction of fist clenches. Individual finger movement was also detectable, showing the potential for prosthesis control of separate digits. Combination of such data therefore enables a classification processor to use both the motion signals and mechanomyographic muscle signals to determine simultaneous patterns of movement of multiple articulating parts of the body.

In another more general example, the motion tracking may be used to provide control signals for input to any computer processor or computer process. The control signals may be derived from the combination of motion sensor data and acoustic sensor data. In one example, such a motion tracking apparatus may determine a first control signal (or set of control signals) corresponding to sensed motion or posture derivable from the motion sensor, and a second control signal (or set of control signals) corresponding to bioacoustic data (e.g. MMG data). The first control signals (or set of control signals) could be comparable to translation motion such as the x-y control of a computer mouse or trackball detected by movement of a user's arm and or wrist. The second control signals (or set of control signals) could be comparable to button clicking motion(s) by flexing one or more fingers, detected by MMG data from the user's fingers. In another example, the motion and posture tracking may be deployed in a wearable gesture control device such as those used for computer game control or virtual reality interface. Other examples are readily devisable.

Figure 7:
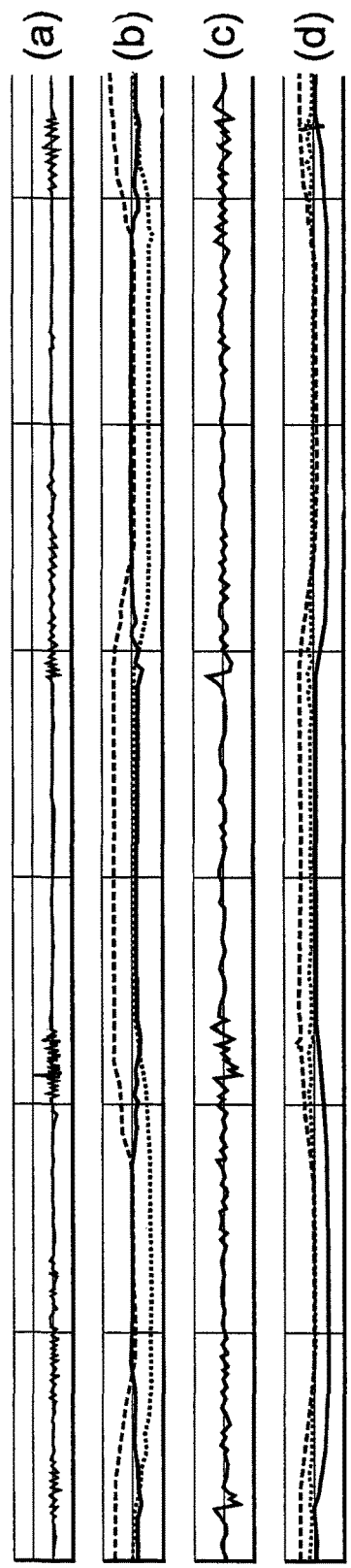
FIG. 7 shows sensor data collected during a sitting to standing task from (a) electromyogram sensing; (b) accelerometer MMG sensing; (c) microphone MMG sensing; and (d) magnetic angular rate and gravity (MARG) sensing.

The results shown in FIG. 7 show muscle detection for EMG (FIG. 7a) compared with MMG data sensed by microphone (FIG. 7c); MMG data sensed by accelerometer (FIG. 7b) and inertial motion sensor data sensed by MARG (FIG. 7d). The MMG data sensed by microphone (FIG. 7c) shows better muscle activity data, i.e. less contaminated by motion. The similarity between the inertial motion data sensor (FIG. 7d) and the MMG accelerometer data also emphasises the benefits of the microphone-based MMG data for reducing motion artefact, particularly for non-isometric muscle activity. For collecting data on isometric contractions, motion is less of an issue.

Figure 8:
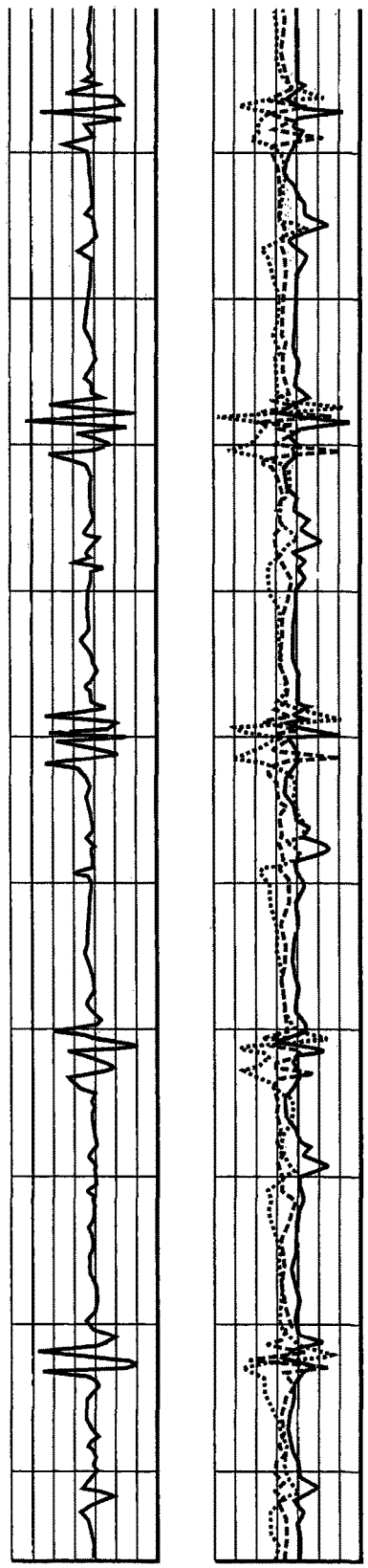
FIG. 8 shows both motion sensor data and mechanomyographic sensor data responsive to a subject walking.
Figure 9:
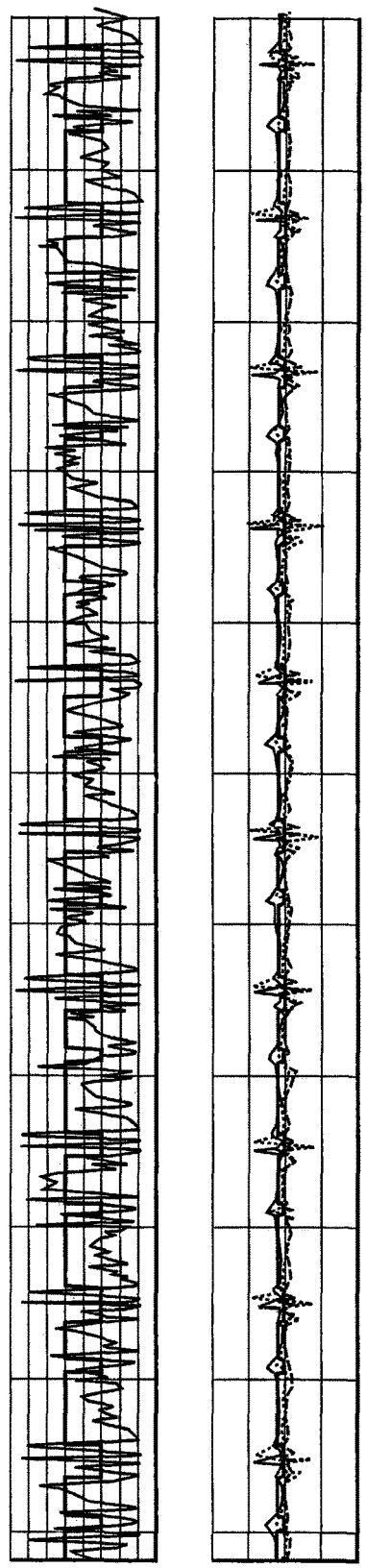
FIG. 9 shows a graph of motion sensor classified stationary and moving periods overlaid on MMG data to further support activity classification.

Synergy of motion sensor data and muscle vibration sensor data can be seen in FIGS. 8 and 9. FIG. 8 shows a five step walk with MMG results in the top graph and motion beneath it. It is clear that increases in amplitude and frequency in the motion data, produced by steps taken when walking, also correspond with MMG data where an increase in activity can also be seen. This indicates a very close relationship of motion and muscle activity. This five step walk shows an onset of muscle activity on every step. FIG. 9 shows a ~10 second segment of data taken from a two hour set of data where a subject is walking. The bottom graph shows inertial data with stationary periods displayed (1 g when stationary, 0 g when active). Likewise, the top graph shows the MMG data but with the same stationary period overlaid (this time 0.2 g is stationary and 0 g is active, however the pattern is the same). When walking analysis is correctly calibrated the stationary periods can be placed over the MMG data to give a representation of when steps were taken in the muscle domain, further supporting walking classification. It can be seen that activity, shown by more sporadic spikes for both motion and muscle activity, are apparent when the stationary period deems the subject to be active, further confirming a successful classification.

Figure 10:
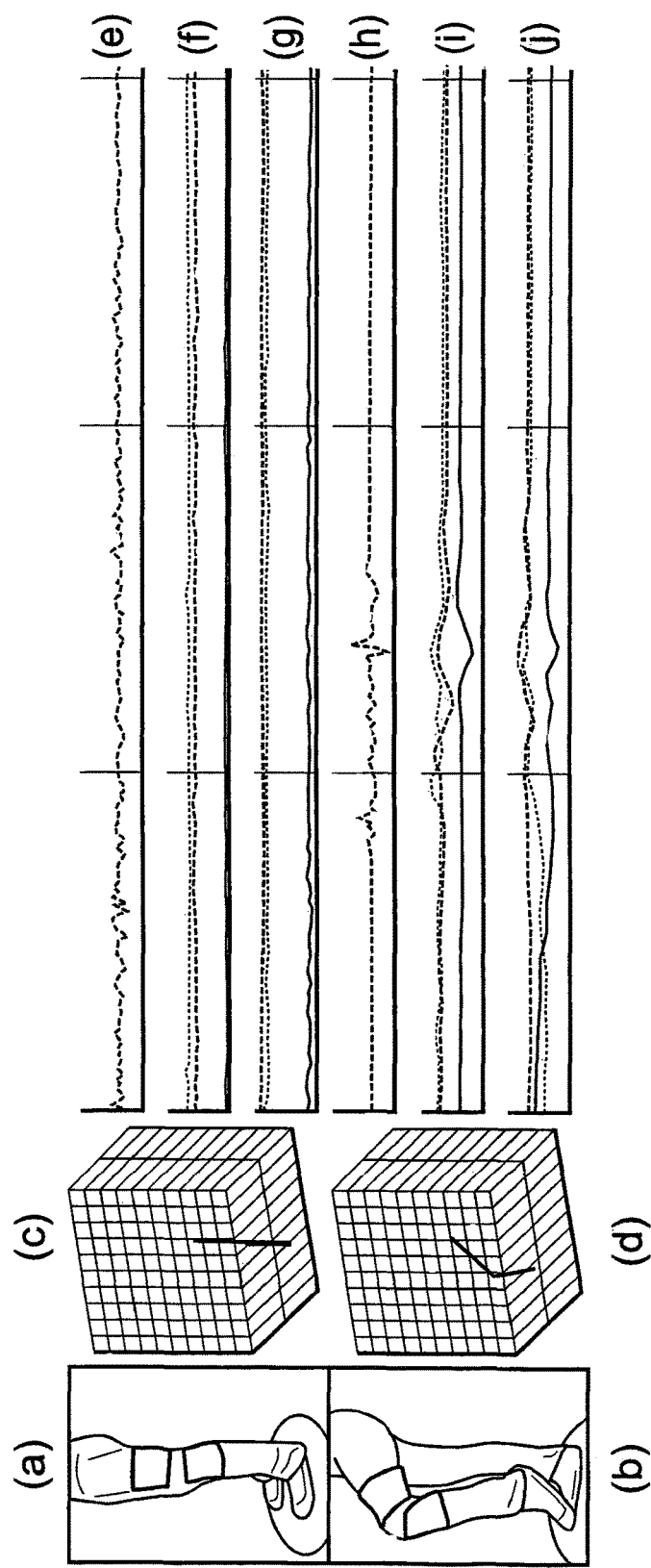
FIG. 10 shows wearable activity sensors provided on both upper and lower leg of a subject together with sensor data received therefrom during standing and a knee-lift task.

Adapting the stick figure model to also show muscle activity gives a new insight into motion and muscle activity acting together. FIG. 10 shows a picture of subject performing one of two tasks: standing upright (FIG. 10a), and knee lifting of a 45 angle (FIG. 10b). FIGS. 10c and 10d respectively show the computational stick figure representation of each task. FIGS. 10e to 10j show the data responses of MMG (FIGS. 10e, 10h) and accelerations of the upper leg (FIGS. 10f, 10i) and lower leg (FIGS. 10g, 10j), for each of the two tasks. The first task, standing upright, was to show the very limited muscle activity (FIG. 10e) and motion (FIGS. 10f, 10g) when no action is being performed. FIG. 10 shows this in the top three images, left to right, of the subject standing still and upright, the computation model also showing a straight non-motion activity, and then the data responses with little movement. The bottom three images, showing the knee lift task (FIG. 10b), also display a picture of a subject lifting the knee, the corresponding model (FIG. 10d), and the data activity (FIGS. 10h to 10j). It is clear to see when the subject lifts the knee from the motion data, but with the MMG data also showing the muscle activity onsets from lifting and dropping the knee.

Embodiments of the sensor apparatus described herein can be lightweight, inexpensive, low power, wireless, easy to use, and give results comparable to standard laboratory techniques. In addition, the sensor apparatus may be able to monitor motion and muscle activity over long periods of time. Results show that some implementations of this technology have a high accuracy when compared with EMG readings. The sensor apparatus may be used in, for example, motion/muscle activity pervasive measurements in the context of rehabilitation monitoring, prosthetic control, and general human activity.

Other embodiments are intentionally within the scope of the accompanying claims.

The invention claimed is:
1. A wearable sensor apparatus comprising:
a motion sensor configured to sense two or three dimensional movement and orientation of the motion sensor;
a vibration sensor configured to sense acoustic vibrations, wherein the vibration sensor comprises an acoustic pressure sensor;
means for attaching the motion sensor and the vibration sensor to a body; and
a classification processor configured to receive motion signals from the motion sensor and to receive muscle vibration signals from the vibration sensor, and to classify a pattern of movement, or a posture of, at least one part of a body on which the wearable sensor apparatus is attached, based on said motion signals, and to identify muscular activity used during said pattern of movement or posture based on the sensed acoustic vibrations.

2. The apparatus of claim 1 in which the motion sensor comprises an inertial measurement unit.

3. The apparatus of claim 1 in which the vibration sensor is configured to sense skeletal muscle vibrations.

4. The apparatus of claim 2 in which the inertial measurement unit comprises one or more of an accelerometer, a gyroscope, and a magnetometer.

5. The apparatus of claim 2 in which the inertial measurement unit is configured to sense rotation of the motion sensor body around at least one axis in space.

6. The apparatus of claim 1 in which the vibration sensor comprises a volumetric chamber closed at one end by a flexible membrane, and a pressure transducer coupled to the chamber distal from the flexible membrane.

7. The apparatus of claim 1 comprising a barometer configured to sense an ambient pressure.

8. The apparatus of claim 1 further comprising a data logging device coupled to receive motion signals from the motion sensor and muscle vibration signals from the vibration sensor, and to store said signals as a function of time.

9. The apparatus of claim 1 wherein the signals from the vibration sensor are mechanomyographic muscle signals and the classification processor is configured to classify a pattern of movement, or a posture of, at least one part of a body on which the wearable sensor apparatus is attached based on the mechanomyographic muscle signals.

10. The apparatus of claim 1 in which the classification processor is configured to use both the motion signals and the muscle vibration signals to determine simultaneous patterns of movement, or postures of, multiple articulating parts of the body on which the wearable sensor apparatus is attached.

11. The apparatus of claim 1 wherein the classification processor is configured to:
separate the signals from the vibration sensor into windowed data;
perform cluster analysis on the windowed data to determine a correlation between the signals from the vibration sensor and a type of activity.

12. The apparatus of claim 11 wherein the cluster analysis comprises determining clusters of the windowed data and comparing one or more properties of the clusters with a corresponding threshold value.

13. The apparatus of claim 12 wherein the one or more properties comprise one or more of: gyroscopic magnitude, peak gyroscopic magnitude, ambient pressure, a cadence of a user and orientation of the motion sensor.

14. The apparatus of claim 7, wherein the classification processor configured to receive motion signals from the motion sensor, to receive an ambient pressure signal from the barometer and to receive signals from the vibration sensor, and to classify a pattern of movement, or a posture of, at least one part of a body on which the wearable sensor apparatus is attached based on the received signals.

15. The apparatus of claim 8 wherein the signals from the muscle vibration signals are mechanomyographic muscle signals.

16. The apparatus of claim 1 in which the classification processor is further configured to determine whether or not the identified muscular activity conforms to a predetermined pattern consistent with the classified pattern of movement.

17. The apparatus of claim 1 further comprising:
 a classification processor configured to receive motion signals from the motion sensor and to receive acoustic signals from the vibration sensor, and to determine when the signals correspond to foetal movement.

18. The apparatus of claim 1 further including an interface module configured to provide output control signals for a computer processor based on the output of the classification processor.

19. The apparatus of claim 1 further including an interface module configured to provide output control signals for a motive apparatus based on the output of the classification processor.

20. The apparatus of claim 19 further including a said motive apparatus.

21. The apparatus of claim 20 in which the motive apparatus comprises a prosthesis or a robotic device.

22. The apparatus of claim 10 wherein the signals from the muscle vibration signals are mechanomyographic muscle signals.

23. The apparatus of claim 1 wherein the signals from the muscle vibration signals are mechanomyographic muscle signals.

24. The apparatus of claim 10 further including an interface module configured to provide output control signals for a computer processor based on the output of the classification processor.

25. The apparatus of claim 10 further including an interface module configured to provide output control signals for a motive apparatus based on the output of the classification processor.

26. The apparatus of claim 25 further including said motive apparatus.

27. The apparatus of claim 26 in which the motive apparatus comprises a prosthesis or a robotic device.

\* \* \* \* \*